United States Patent
De Jong et al.

(10) Patent No.: US 9,582,055 B2
(45) Date of Patent: *Feb. 28, 2017

(54) MEDICAL COMMUNICATION HUB AND ASSOCIATED METHODS

(71) Applicant: Volcano Corporation, San Diego, CA (US)

(72) Inventors: Duane De Jong, Elk Grove, CA (US); Gerald L. Litzza, Sacramento, CA (US); Dennis Schuerkamp, North Highlands, CA (US); Paul Michael Hoseit, El Dorado Hills, CA (US)

(73) Assignee: Volcano Corporation, San Diego, CA (US)

( * ) Notice: Subject to any disclaimer, the term of this patent is extended or adjusted under 35 U.S.C. 154(b) by 313 days.

This patent is subject to a terminal disclaimer.

(21) Appl. No.: 14/176,876

(22) Filed: Feb. 10, 2014

(65) Prior Publication Data

US 2014/0218210 A1    Aug. 7, 2014

Related U.S. Application Data

(63) Continuation of application No. 14/238,026, filed as application No. PCT/US2012/052241 on Aug. 24, 2012.

(60) Provisional application No. 61/526,990, filed on Aug. 24, 2011.

(51) Int. Cl.
| | |
|---|---|
| A61B 5/00 | (2006.01) |
| G06F 1/26 | (2006.01) |
| A61B 8/00 | (2006.01) |
| G06F 13/40 | (2006.01) |
| G08C 19/16 | (2006.01) |
| G08C 19/00 | (2006.01) |

(52) U.S. Cl.
CPC ............ *G06F 1/266* (2013.01); *A61B 5/0066* (2013.01); *A61B 5/742* (2013.01); *A61B 8/565* (2013.01); *G06F 13/4081* (2013.01); *G08C 19/00* (2013.01); *G08C 19/16* (2013.01); *A61B 2560/0204* (2013.01)

(58) Field of Classification Search
CPC .......... A61B 2560/0204; A61B 5/0066; A61B 5/742; A61B 8/565; G06F 13/4081; G08C 19/00; G08C 19/16
USPC ..................................................... 340/870.02
See application file for complete search history.

(56) References Cited

U.S. PATENT DOCUMENTS

| | | | |
|---|---|---|---|
| 2003/0130590 A1* | 7/2003 | Bui ...................... | A61B 5/0002 600/537 |
| 2005/0146431 A1* | 7/2005 | Hastings ................ | A61B 5/002 340/539.12 |
| 2008/0001735 A1* | 1/2008 | Tran .................... | G06F 19/3418 340/539.22 |

* cited by examiner

Primary Examiner — Omer S Khan

(57) ABSTRACT

A medical sensing system including a data acquisition module operable to receive patient data from a medical sensing device, the data acquisition module being operable to packetize the patient data, a processing module operable to process the packetized first patient data, a user interface module operable to present the processed packetized patient data within a graphical user interface, and a message queue module in communication with the data acquisition module, processing module, and user interface module, the message queue module being operable to receive the packetized patient data from the modules, temporarily store the packetized patient data, and make the packetized patient data available for retrieval by the modules.

21 Claims, 17 Drawing Sheets

MEDICAL COMMUNICATION HUB AND ASSOCIATED METHODS

CROSS-REFERENCE TO RELATED APPLICATIONS

The present application is a continuation of U.S. patent application Ser. No. 14/238,026, filed Feb. 10, 2014, which is a U.S. national stage application Patent Cooperation Treaty Application No. PCT/US2012/052241, filed Aug. 24, 2012, which claims priority to and the benefit of U.S. Provisional Patent Application No. 61/526,990, filed Aug. 24, 2011, each of which is hereby incorporated by reference in its entirety.

TECHNICAL FIELD

Embodiments of the present disclosure relate generally to the field of medical devices and, more particularly, to a medical communication system and associated methods of use.

BACKGROUND

Innovations in diagnosing and verifying the level of success of treatment of disease have migrated from solely using external imaging processes to now including internal diagnostic processes as well. In particular, diagnostic equipment and processes have been developed for diagnosing vasculature blockages and other vasculature disease by means of ultra-miniature sensors placed upon the distal end of a flexible elongate member such as a catheter, or a guide wire used for catheterization procedures. For example, known medical sensing techniques include angiography, intravascular ultrasound (IVUS), forward looking IVUS (FL-IVUS), fractional flow reserve (FFR) determination, a coronary flow reserve (CFR) determination, optical coherence tomography (OCT), trans-esophageal echocardiography, and image-guided therapy. Each of these techniques may be better suited for different diagnostic situations. To increase the chance of successful treatment, health care facilities may have a multitude of imaging and sensing modalities on hand in a catheter lab during a procedure. However, each imaging modality in a catheter lab traditionally requires its own special-purpose diagnostic equipment. For instance, an imaging modality may require a catheter, a patient interface module (PIM), a user control interface, a display, a specialized power unit, and a processing unit such as a customized personal computer. Traditionally, all of this equipment is located in the catheter room itself during a procedure and depends on a substantial wiring infrastructure for data transport and dependable power. Physical space is typically at a premium in catheter labs and each additional imaging modality employed in a catheter lab complicates the pre-procedure setup and limits the movement of health care professionals during procedures. For example, typically, each additional imaging modality may require its own communication cable and its own power cable. These cable assemblies are often coiled under patient tables and are prone to being damaged from either being stepped on by personnel or equipment rolling over them. Cleaning the cables after a procedure is also very time consuming and difficult.

While the existing devices and methods have been generally adequate for their intended purposes, they have not been entirely satisfactory in all respects. The medical sensing systems and associated methods of the present disclosure overcome one or more of the shortcomings of the prior art.

SUMMARY

In one exemplary aspect, the present disclosure is directed to a powered medical communication hub. The hub includes a housing and a rear interface assembly disposed at a distal end of the housing. The rear interface assembly includes a first data link configured to transmit first medical data associated with a first modality to a processing system and a power link configured to receive a first amount of power. The hub also includes a power distribution module disposed within the housing, electrically coupled to the power link, and configured to convert the first amount of power into a plurality of power levels, and a forward interface assembly disposed at a proximal end of the housing, the forward interface assembly including a first connector communicatively coupled to the first data link and electrically coupled to the power distribution module, the first connector being configured to provide a first medical sensing device coupled thereto with a second amount of power equal to one of the plurality of power levels and receive the first medical data from the first medical sensing device.

In some instances, the housing may be fluid resistant and an interface between the rear interface assembly and the housing and an interface between the front interface assembly and the housing may be fluid resistant. Also, in some instances, the second amount of power may be different than the first amount of power. Additionally, in some instances, the front interface assembly may include a second connector electrically coupled to the power distribution module, the second connector being configured to provide a second medical sensing device coupled thereto with a third amount of power equal to one of the plurality of power levels and receive second medical data associated with a second modality different from the first modality from the second medical sensing device.

In another exemplary aspect, the present disclosure is directed to a medical communication system including a powered medical communication hub having a mounting portion thereon. The hub includes a plurality of connectors, each connector in the plurality of connectors being configured to receive medical data associated with a different medical sensing modality and to provide power to a medical sensing device coupled thereto and a rear interface assembly configured to receive a plurality of cables, the cables communicatively and electrically coupling the hub to a processing system. The system also includes mounting means releasably coupled to the mounting portion of the powered medical communication hub, the mounting means being configured to mount the powered medical communication hub within a medical environment and a cable protection assembly releasably coupled to the rear interface assembly of the powered medical communication hub, the plurality of cables extending through the cable protection assembly.

In some instances, the cable protection assembly may include an elongate and flexible housing enclosing the cables therein. Also, in other instances, the mounting means may include a rail clamp configured to releasably couple to a rail in a medical environment. In yet another exemplary aspect, the present disclosure is directed to a method of collecting medical sensing data including receiving, at a powered medical communication hub, a first amount of power from a power source, converting, with a power distribution module in the powered medical communication hub, the first amount of power into a plurality of power levels, providing, with the powered medical communication hub, a second amount of power equal to one of the plurality of power levels to a first medical sensing device, receiving, at the powered medical communication hub, first medical data associated with a first modality from the first medical sensing device, and transmitting, with the powered medical communication hub, the first medical data to a processing system.

In some instances, the method of collecting medical sensing data may include providing, with the powered medical communication hub, a third amount of power equal to one of the plurality of power levels to a second medical sensing device, receiving, at the powered medical communication hub, second medical data associated with a second modality different from the first modality from the second medical sensing device, and transmitting, with the powered medical communication hub, the second medical data to the processing system.

In one exemplary aspect, the present disclosure is directed to a medical sensing system. The medical sensing system includes a first data acquisition module associated with a first medical sensing modality and operable to receive first patient data associated with the first medical sensing modality from a first medical sensing device, the first data acquisition module being operable to packetize the first patient data and being one of a plurality of data acquisition modules. The system also includes a first processing module associated with the first medical sensing modality and operable to process the packetized first patient data, the first processing module being one of a plurality of processing modules. Further, the system includes a first user interface module associated with the first medical sensing modality and operable to present the processed packetized first patient data within a first graphical user interface, the first user interface module being one of a plurality of user interface modules. Additionally, the system includes a message queue module in communication with the first data acquisition module, first processing module, and first user interface module, the message queue module being operable to receive the packetized first patient data from the modules, temporarily store the packetized first patient data, and make the packetized first patient data available for retrieval by the modules.

In some instances, the medical sensing system further includes a second data acquisition module associated with a second medical sensing modality and operable to receive second patient data associated with the second medical sensing modality from a second medical sensing device, the second data acquisition module being operable to packetize the second patient data and being one of the plurality of data acquisition modules. Further, in some instances the system includes a second processing module associated with the second medical sensing modality and operable to process the packetized second patient data, the second processing module being one of the plurality of processing modules. Additionally, in some instances, the system includes a second user interface module associated with the second medical sensing modality and operable to present the processed packetized second patient data within a second graphical user interface, the second user interface module being one of the plurality of user interface modules.

In another exemplary aspect, the present disclosure is directed to a medical sensing system. The medical sensing system includes a first data acquisition module associated with a first medical sensing modality and operable to receive first patient data associated with the first medical sensing modality from a first medical sensing device, the first acquisition module being further operable to create a first plurality of messages containing the first patient data. The system also includes a message queue module operable to receive and temporarily store the first plurality of messages from the first data acquisition module. Further, the system includes a first processing module associated with the first medical sensing modality and operable to retrieve the first plurality of messages from the message queue module, process the first patient data within the first plurality of messages, and transmit a second plurality of messages containing the processed first patient data to the message queue module. Additionally, the system includes a first user interface module associated with the first medical sensing modality and operable to retrieve the second plurality of messages from the message queue module and present the processed first patient data within a first graphical user interface.

In some instances, the first data acquisition module of the medical sensing system is one of a plurality of acquisition modules, the first processing module is one of a plurality of processing modules, and the first user interface module is one of a plurality of user interface modules.

In another exemplary aspect, the present disclosure is directed to a method of processing medical sensing data. The method of processing medical sensing data includes receiving first patient data from a first medical sensing device, the first patient data being associated with a first medical sensing modality and creating a first plurality of messages wherein each message in the first plurality of messages contains a portion of the first patient data. The method also includes queuing the first plurality of messages on a message queue, retrieving the first plurality of messages from the message queue, and processing the first patient data contained in the first plurality of messages. Further, the method includes creating a second plurality of messages wherein each message in the second plurality of messages contains a portion of the processed first patient data and queuing the second plurality of messages on the message queue. Additionally, the method includes retrieving the second plurality of messages from the message queue and rendering, within a first graphical user interface, the processed first patient data contained in the second plurality of messages.

In another exemplary aspect, the present disclosure is directed to a medical sensing system including a computing device operable to receive first medical data associated with a first medical sensing modality from a first medical sensing device. The computing device includes a processor and a non-transitory computer-readable medium communicatively coupled to the processor and including a plurality of instructions stored therein and executable by the processor. The plurality of instructions include instructions for receiving first patient data from a first medical sensing device, the first patient data being associated with a first medical sensing modality. The plurality of instructions also include instructions for creating a first plurality of messages wherein each message in the first plurality of messages contains a portion of the first patient data. Further, plurality of instructions include instructions for queuing the first plurality of messages on a message queue, instructions for retrieving the first plurality of messages from the message queue, and instructions for processing the first patient data contained in the first plurality of messages. The plurality of instructions also include instructions for creating a second plurality of messages wherein each message in the second plurality of messages contains a portion of the processed first patient data and instructions for queuing the second plurality of messages on the message queue. Additionally, the plurality of instructions include instructions for retrieving the second plurality of messages from the message queue and instructions for rendering, within a first graphical user interface, the processed first patient data contained in the second plurality of messages.

DETAILED DESCRIPTION

Figure 1:
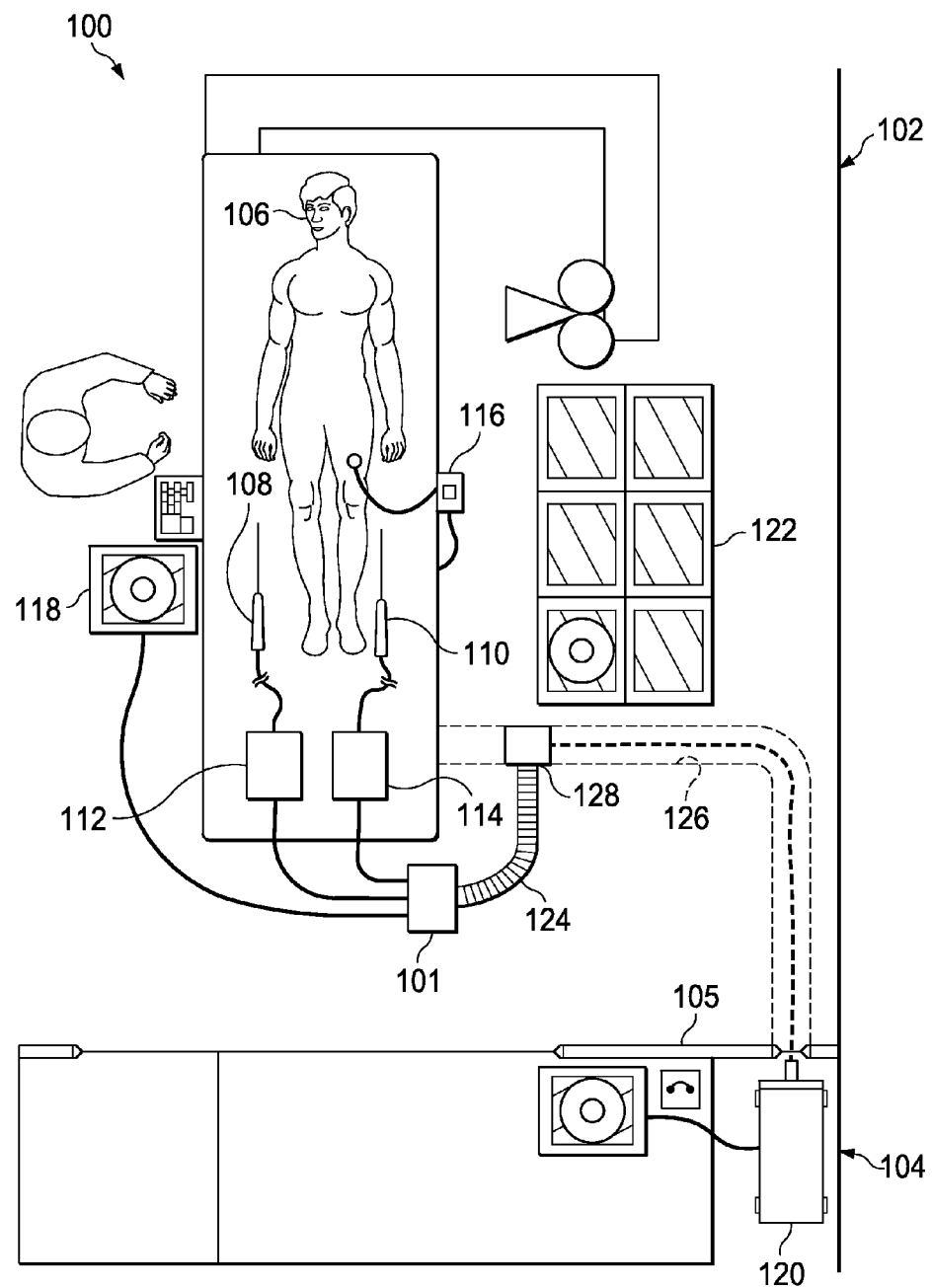
FIG. 1 is a schematic drawing depicting a medical sensing communication system including a powered medical communication hub according to one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications in the described devices, instruments, methods, and any further application of the principles of the disclosure as described herein are contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure.

FIG. 1 is a schematic drawing depicting a medical sensing communication system 100 including a powered medical communication hub 101. The medical sensing communication system 100 is a data collection solution for multiple modality medical sensing. Generally, in the system 100, the hub 101 is a central unit that connects to a plurality of medical sensing-related tools, distributes power to the plurality of tools, and facilitates communication between the tools and a processing workstation and/or data network. In one embodiment, the communication system 100 may be utilized to collect data from medical sensing devices and transmit it to computing resources, where it is processed and returned.

In the illustrated embodiment, the medical sensing communication system 100 is deployed in a catheter lab 102 having a separate control room 104 isolated by an intervening wall 105. In other embodiments, however, the medical sensing communication system 100 may be deployed in an operating room, diagnostic room, or other medical environment used to perform any number of patient procedures. The catheter lab 102 includes a sterile field but its associated control room 104 may or may not be sterile depending on the requirements of a procedure and/or health care facility. The catheter lab and control room may be used to perform on a patient any number of medical sensing procedures such as angiography, intravascular ultrasound (IVUS), virtual histology (VH), forward looking IVUS (FL-IVUS), intravascular photoacoustic (IVPA) imaging, a fractional flow reserve (FFR) determination, a functional measurement determination, a coronary flow reserve (CFR) determination, optical coherence tomography (OCT), computed tomography, intracardiac echocardiography (ICE), forward-looking ICE (FLICE), intravascular palpography, transesophageal ultrasound, or any other medical sensing modalities known in the art. For example, in catheter lab 102 a patient 106 may be undergoing a multi-modality procedure, in which IVUS data will be collected with an IVUS catheter 108 and OCT data will be collected with an OCT catheter 110. The IVUS catheter 108 may include one or more sensors such as a phased-array transducer. In some embodiments, the IVUS catheter 108 may be capable of multi-modality sensing such as IVUS and IVPA sensing. The OCT catheter 110 may include one or more optical sensors.

The communication system 100 includes a number of interconnected medical sensing-related tools in the catheter lab 102 and control room 104 to facilitate this multi-modality workflow procedure, including an IVUS patient interface module (PIM) 112, an OCT PIM 114, an electrocardiogram (ECG) device 116, a bedside control surface 118, a processing system 120, and a boom display 122. The hub 101 in the catheter lab 102 consolidates the multitude of cables extending from these medical sensing-related tools and communicatively couples them to the processing system 120. That is, the hub 101 is an intermediary through which the tools in the catheter lab 102 connect to the processing system 120. In general, the hub 101 is coupled to the processing system 120 via a plurality of power and communication cables. To alleviate the problems associated with loose cabling in a crowded medical working environment, the cables coupling the hub 101 to the processing system 120 extend through a protective hose 124 and a trench 126 in the floor of the catheter lab 102. The cables enter the trench 126 through a trench entry port 128. In this manner, the cables are aggregated and protected the entirety of the distance from the hub 101 to the processing system 120. Of course, the cabling between the hub 101 and processing system 120 may be oriented in many other configurations depending on the specific catheter lab configuration. For instance, the cabling may extend through the protective hose 124 and enter a wall or a ceiling through a termination plate before travelling to the processing system. In the illustrated embodiment, the hub 101 is mounted on the floor near the patient 106 to reduce the amount of cabling located in high-traffic areas near the patient. In some instances, the hub 101 may be located in the sterile field surrounding the patient 106. The hub 101 and its associated cabling and mounting solutions will be described in greater detail in association with FIGS. 2-12.

In the illustrated embodiment, the processing system 120 is a computer workstation with the hardware and software to acquire, process, and display multi-modality medical sensing data, but in other embodiments, the processing system 120 may be any other type of computing system operable to process medical data or assist in computer aided surgery (CAS). In the embodiments in which processing system 120 is a computer workstation, the system includes at least a processor such as a microcontroller or a dedicated central processing unit (CPU), a non-transitory computer-readable storage medium such as a hard drive, random access memory (RAM), and/or compact disk read only memory (CD-ROM), a video controller such as a graphics processing unit (GPU), and a network communication device such as an Ethernet controller. U.S. Patent Application No. 61/473,570, entitled "MULTI-MODALITY MEDICAL SENSING SYSTEM AND METHOD", discloses a computing resource capable of processing multi-modality medical sensing data and is hereby incorporated by reference in its entirety.

As mentioned above, the ECG device 116 is also communicatively coupled to hub 101 via a wired or wireless connection. The ECG device 116 is operable to transmit electrocardiogram signals from patient 106 to the hub 101. In some embodiments, the hub 101 may be operable to synchronize data collection with the catheters 108 and 110 using the ECG signals from the ECG 116.

The bedside control surface 118 is also communicatively coupled to the hub 101 and provides user control of the particular medical sensing modality (or modalities) being used to diagnose the patient 106. In the current embodiment, the bedside control surface 118 is a touch screen that provides user controls and diagnostic images on a single surface. In alternative embodiments, however, the bedside control surface 118 may include both a non-interactive display and separate controls such as physical buttons and/or a joystick. In the illustrated embodiment, the bedside control surface 118 and hub 101 communicate over a wired connection such as a standard copper link but, alternatively, the control surface 118 and hub 101 may communicate wirelessly. The bedside control surface 118 includes an integrated processing unit to drive a graphical user interface (GUI)-based workflow presented on the touch screen. U.S. Patent Application No. 61/473,591, entitled "DISTRIBUTED MEDICAL SENSING SYSTEM AND METHOD" and filed on Apr. 8, 2011, discloses a bedside control surface that executes GUI-based workflows using a software framework and is hereby incorporated by reference in its entirety.

The system 100 further includes a boom display 122. The boom display 122 may include one or more monitors capable of displaying information associated with a medical sensing procedure. In the illustrated embodiment, the boom display 122 is coupled to, powered, and driven by the hub 101.

Figure 2A:
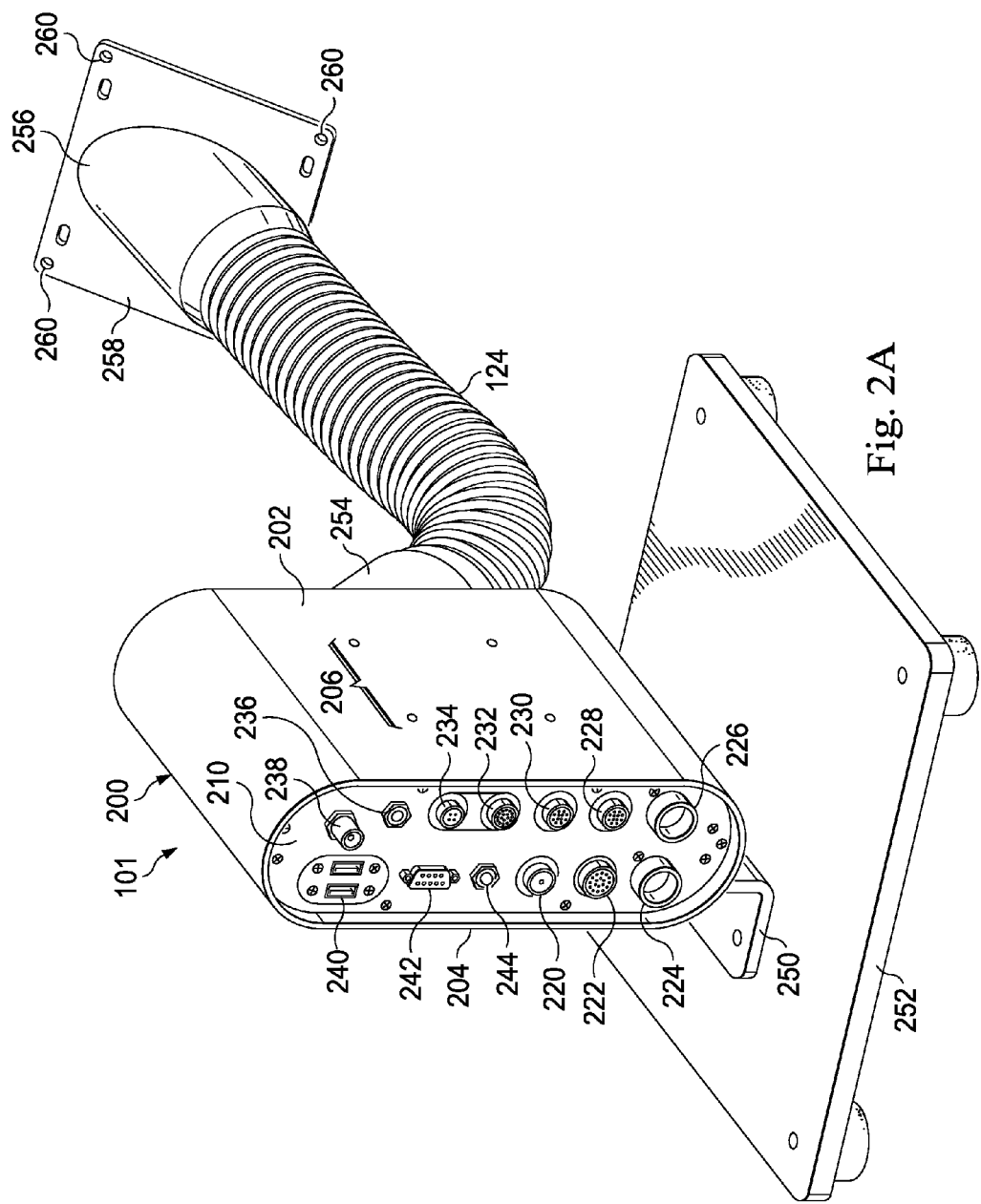
FIG. 2A is a diagrammatic front perspective view of the powered medical communication hub of FIG. 1 installed in a catheter lab.
Figure 2B:
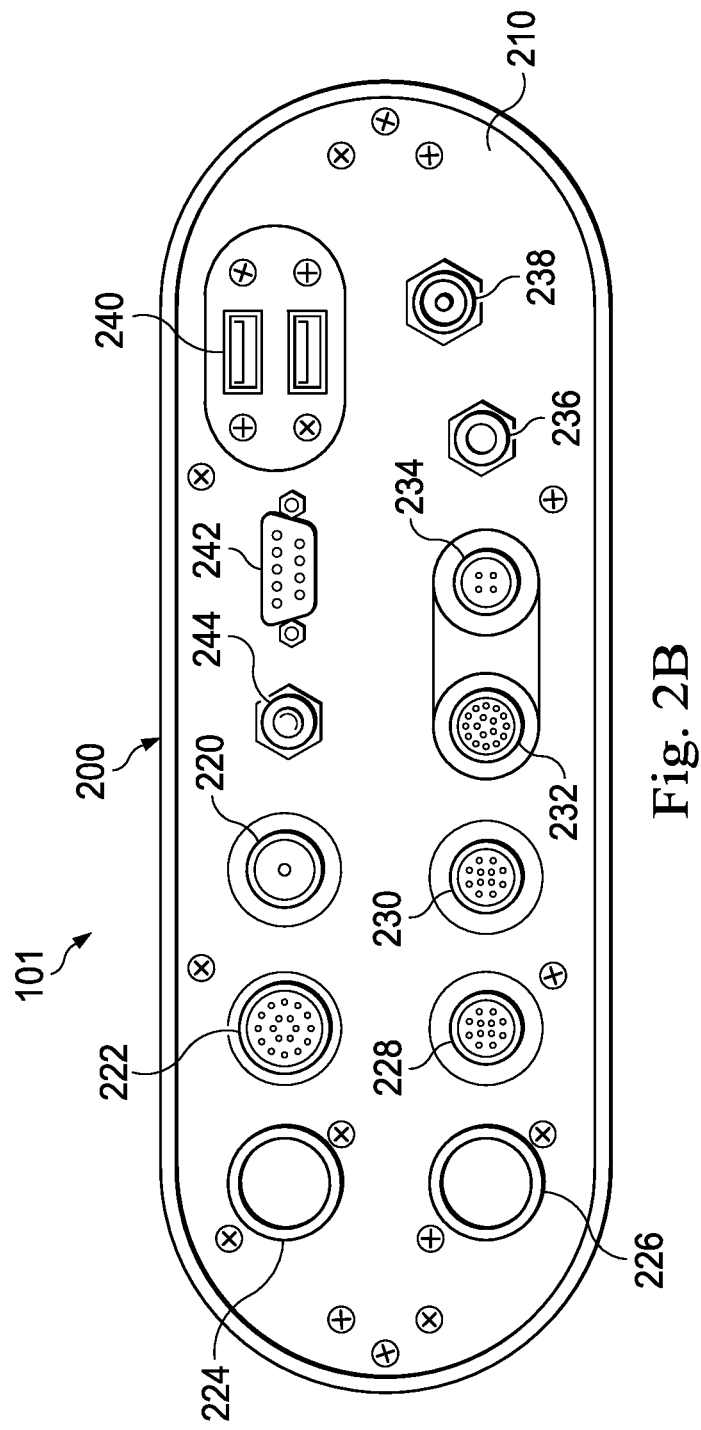
FIG. 2B is a diagrammatic front close-up view of the powered medical communication hub of FIG. 1.
Figure 3:
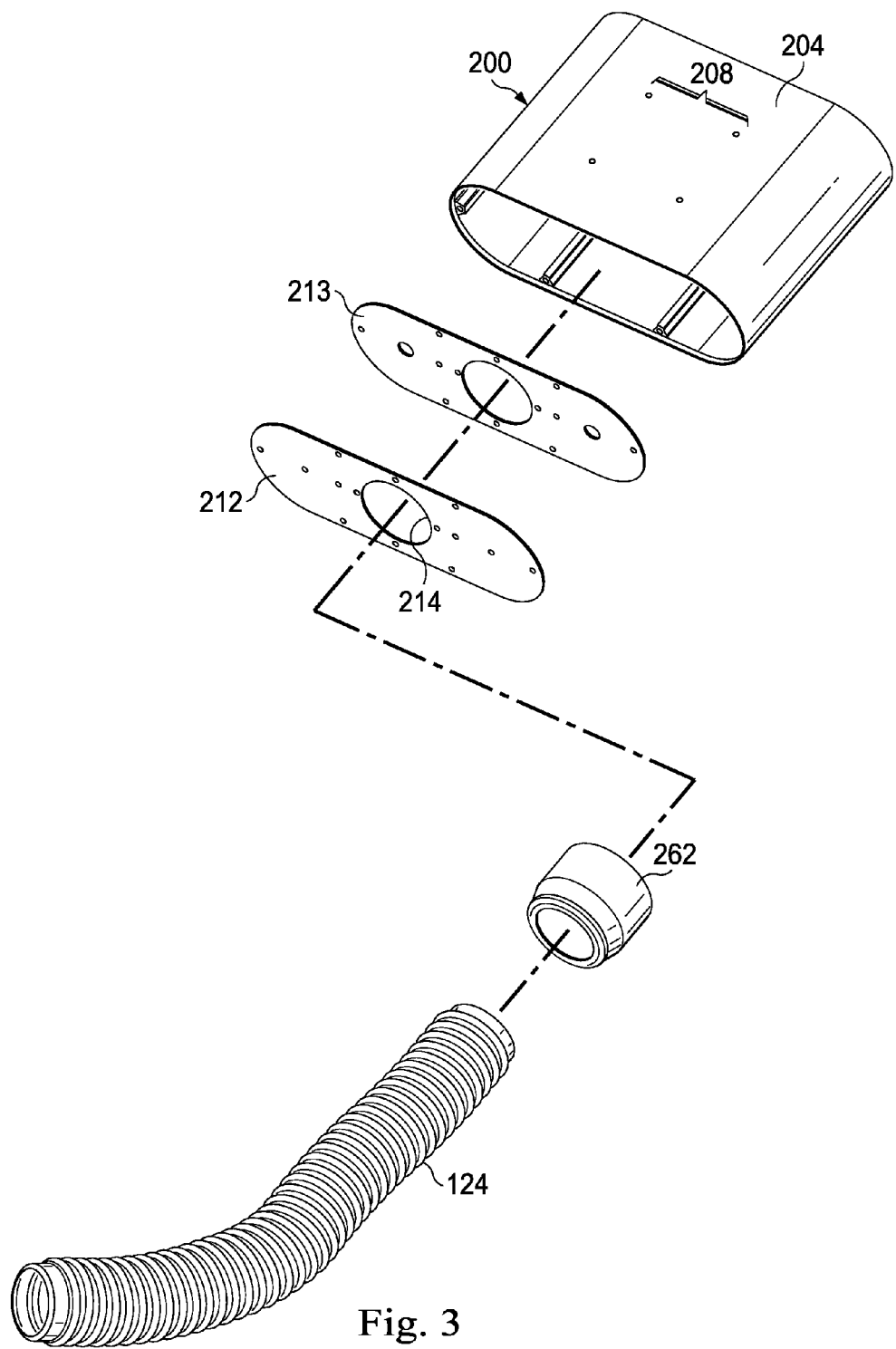
FIG. 3 is a diagrammatic rear perspective exploded view of portions of the powered medical communication hub of FIG. 1.

With reference now to FIGS. 2A, 2B, and 3, illustrated is an aspect of the medical sensing communication system 100. Specifically, FIG. 2A is a diagrammatic front perspective view of the powered medical communication hub 101 of FIG. 1 installed in a medical environment such as catheter lab 102, and FIG. 2B is a diagrammatic front close-up view of the hub 101. FIG. 3 is a diagrammatic rear perspective exploded view of portions of the hub 101. As mentioned above, the hub 101 is a intermediary through which the medical sensing-related tools receive power and communicate with processing system 120. In one general aspect, the hub 101 is operable to provide power and instructions to medical sensing devices and transfer medical sensing data from connected medical sensing devices such as the IVUS PIM 112 and OCT PIM 114 to remote computing resources such as processing system 120 to be processed. Once processed, the medical sensing data may be returned to the hub 101, where it is routed to the control surface 118 and boom display 122 to be displayed and analyzed by clinicians.

The hub 101 includes a cylinder-like housing 200. In the illustrated embodiment, the housing 200 is constructed of a impact-resistant and fluid-resistant metal and has a height of approximately 3.5 inches, a width of approximately 10 inches, and a depth of approximately 8 inches. In alternative embodiments, the housing 200 may be constructed of a different suitable material and/or be of different dimensions. The housing 200 includes a bottom mounting surface 202 and a top mounting surface 204, both of which are planar. The bottom mounting surface 202 includes a set of threaded mounting apertures 206 and the top mounting surface 204 includes a set of threaded mounting apertures 208. As will be described in association with FIGS. 7-10, any number of mounting brackets may be releasably coupled to the housing 200 using either set of threaded mounting apertures 206 and 208. In the illustrated embodiment, each set of mounting apertures is configured to conform to the Video Electronics Standards Association (VESA) MIS-D hole mount pattern. In alternative embodiments, the mounting apertures 206 and 208 may conform to a different standard or may conform to a proprietary pattern. Further, the mounting surfaces 202 and 204 may alternatively include different mounting solutions such as channels, slots, clips, or magnetic elements.

The hub 101 further includes a front interface panel 210 coupled to the front of the housing 200 and a rear interface panel 212 coupled to the rear of the housing 200. Each of the interface panels 210 and 212 includes a complementary gasket 213 disposed on the side facing the housing 200 such that when they are secured to the housing 200 as shown in FIG. 2A they create a fluid-resistant seal. The gaskets 213 may be formed of rubber, silicone, or other sealing material. In one embodiment, the hub 101 may have a rating of IPX4 against fluid ingress as defined by the International Electrotechnical Commission (IEC) standard 60529. In other embodiments in which the hub may be used in different environments, the hub may have a different fluid ingress rating. As shown in FIG. 3, the rear interface panel 212 includes a cable aperture 214 through which cables extending from the hub 101 to the processing system 120 may pass. As shown in FIG. 2B, the front interface panel 210 of the hub 101 includes a plurality of connectors to which a plurality of medical sensing-related tools may connect. In the illustrated embodiment, the front panel 210 includes: an IVUS PIM connector 220 with conductive contacts configured to transfer power, ground, data, and control signals; a functional measurement (FM) tool connector 222 with conductive contacts configured to transfer power, ground, data and control signals; an first fiber optic connector 224 and a second fiber optic connector 226 each configured to pass power, ground, and light-based data signals; an OCT PIM connector 228 with conductive contacts configured to transfer 48 volts DC, ground, and Ethernet-based data; a bedside control surface connector 230 with conductive contacts configured to transfer 12 volts DC, ground, and Ethernet-based data; a FLIVUS PIM connector 232 with conductive contacts configured to transfer 48 volts DC, ground, and Universal Serial Bus (USB)-based data; and a FLIVUS footswitch connector 234 with conductive contacts configured to transfer foot-actuated control signals. The connectors 220, 222, 228, 230, 232, and 234 are push-pull ring style connectors that are configured to allow for one-handed connection and disconnection of cables. Further, the connectors are fluid-resistant (sealed), color-coded for easy identification, and keyed differently, for example in shape and pin-count, so as prevent misconnected cables. For example, as shown in FIG. 2B, the FM tool connector includes 18 pin holes in a circular configuration, but the bedside control surface connector includes 12 pin holes in a linear configuration. In the illustrated embodiment, the connectors 228, 230, 232, and 234 are JBX series connectors commercially available from Souriau SAS of Versailles, France. However, in alternative embodiments, other commercially-available or proprietary connectors may be utilized and the connectors may be configured to include any number of additional features. Although the connectors 220, 222, 224, 226, 228, 230, 232, and 234 as-labeled are associated with specific modalities, it is contemplated that medical tools associated with additional and/or different modalities may connect to one or more of the connectors provided that the medical tools' connectors are compatible (i.e. number of pins, shape).

The front panel 210 further includes an auxiliary power connector 236 configured to provide 24 volts DC, a ECG/aortic device connector 238, two USB connectors 240, and a VGA display connector 242. In one catheter lab configuration, the auxiliary power connector 236 may provide power and the VGA display connector 242 may provide a video signal to a bedside display monitor such as the boom display 122. Further, the USB connectors 240 may couple to and receive control signals from bedside controller devices such as joysticks, touchpads, hand gesture/motion capture input devices, or any other suitable controller devices. In the illustrated embodiment, because the USB connectors 240 and the VGA display connector 242 are standardized, it is contemplated that any number of USB-based and VGA-based tools may communicate with the processing system 120 via the hub 101. Additionally, the USB connectors 240 may be fluid-resistant. Further, in alternative embodiments, the VGA display connector 242 may be another type of display connector such as a DVI connector, an HDMI connector, a DisplayPort connector, an S-Video connector, or other video-based connector, and the USB connectors 240 may be other types of data ports such as IEEE 1394 (FireWire), Thunderbolt, serial, parallel, eSATA, or proprietary connectors. Additionally, the front panel 210 includes an LED indicator 244 configured to indicate when the hub 101 is powered on. The front interface panel 210 and the connectors 220, 222, 224, 226, 228, 230, 232, 234, 236, 238, 240, and 242 may together be considered a forward interface assembly.

As mentioned above, FIG. 2A shows the hub 101 installed in one example configuration in a medical environment such as catheter lab 102. Specifically, a vertical mounting bracket 250 is coupled to the top mounting surface 204 via the set of threaded mounting apertures 208. The mounting bracket 250 is in turn mounted to a floor stand 252, which is configured to sit on the floor of a catheter lab with a plurality of stabilizing feet. Further, cables extending from the hub 101 to the processing system 120 exit the hub 101 through the aperture 214 in the rear panel 212 and extend through an angled coupler 254, the flexible protective hose 124, a second angled coupler 256, and an aperture in a termination plate 258. The angled coupler 254 releasably couples to the rear panel 212 and includes a rubber seal around its periphery such that when it is coupled to the panel the interface between the coupler and the panel is fluid-resistant. The flexible protective hose 124 is configured to protect the cables extending therethrough and may be resistant to bodily fluids and cleaning chemicals typically found in medical environments. The flexible protective hose 124 is further pliable such that it may be routed in a convenient manner in a catheter lab. The termination plate 258 includes an aperture sized to approximately match the diameter of the second angled coupler 256, and also includes a set of mounting apertures 260 configured in a standardized pattern on the face of the plate. The mounting apertures 260 permit the plate 258 to be mounted around an aperture (e.g. a wall exit point, floor exit point, etc) through which the hub-connected cables exit the catheter lab. In the illustrated embodiment, the termination plate 258 and the set of mounting apertures 260 conform to the GE Termination standard. However, in other embodiments, the termination plate 258 and apertures 260 may conform to another standard such the Phillips Termination standard, the double gang standard, or the single gang standard. As shown in FIG. 3, a straight coupler 262 may also be releasably coupled to the rear panel 212 and the flexible protective hose 124. The straight coupler 262 directs the protective hose 124 away from the hub 101 at a different angle than the angled coupler 254 to provide for additional placement options in a catheter lab or other medical environment. The angled coupler 254 or straight coupler 262, flexible protective hose 124, and second angled coupler 256 may together be considered a cable protection assembly.

Figure 4:
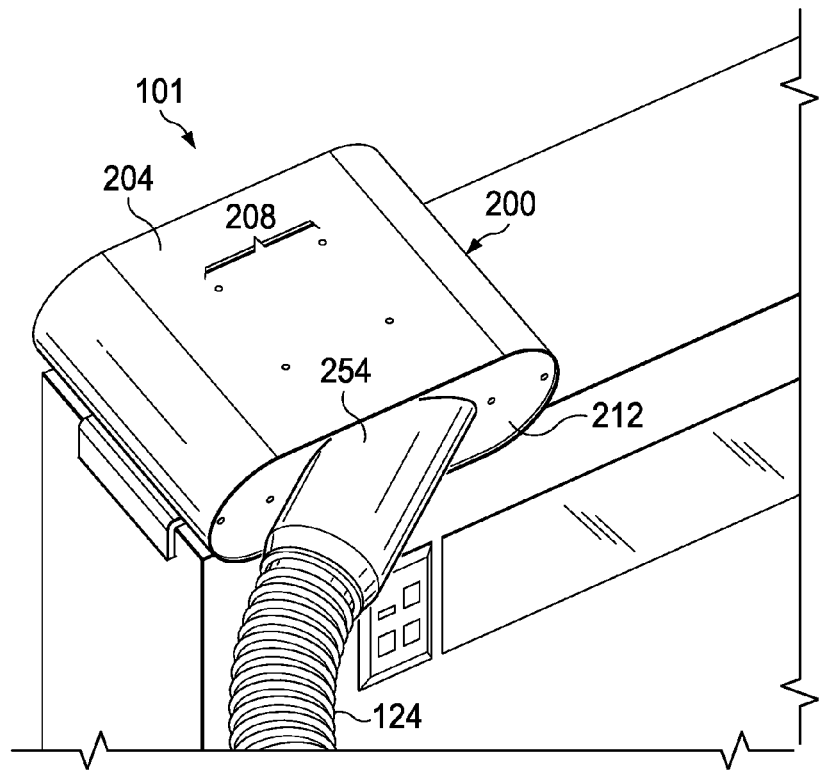
FIG. 4 is a rear perspective view of a powered medical communication hub with an angled coupler attached thereto.
Figure 5:
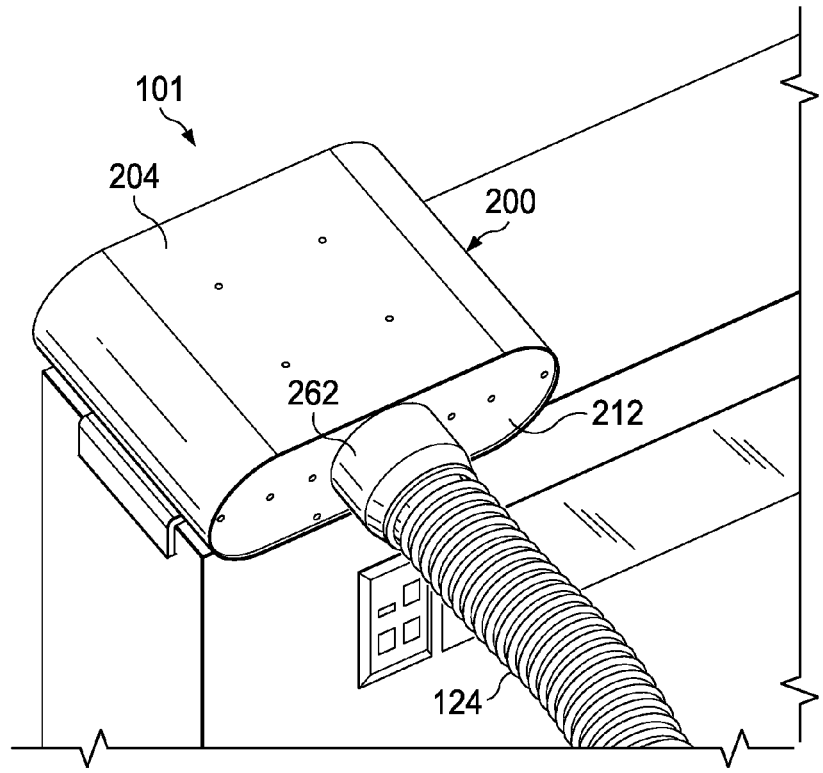
FIG. 5 is a rear perspective view of a powered medical communication hub with a straight coupler attached thereto.
Figure 12:
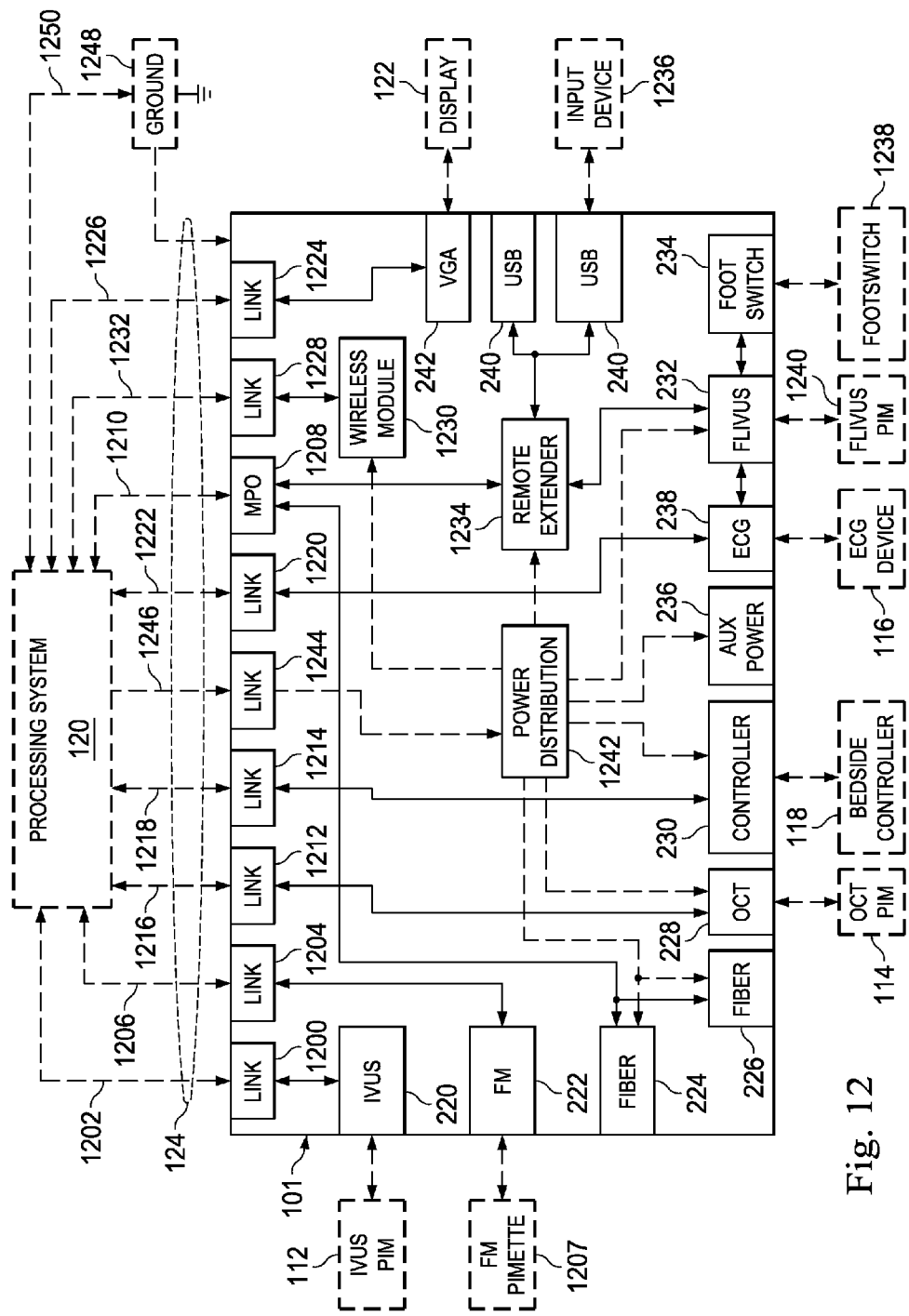
FIG. 12 is a functional block diagram of an embodiment of a powered medical communication hub.

With reference now to FIGS. 4 and 5, illustrated are different configurations of the medical communication system 100 in a medical environment. Specifically, FIG. 4 is a rear perspective view of the hub 101 with the angled coupler 254 coupled to the rear panel 212, and FIG. 5 is a rear perspective view of the hub 101 with the straight coupler 262 coupled to the rear panel 212. As shown by FIGS. 4 and 5, the couplers 254 and 262 direct the flexible protective hose 124 away from the hub 101 at different angles. As shown, all cable-based connections to the rear of the hub 101 including power and communications are contained within the flexible hose 124. Examples of the cables exiting the rear of the hub 101 within the hose 124 are shown in FIG. 12.

Figure 6:
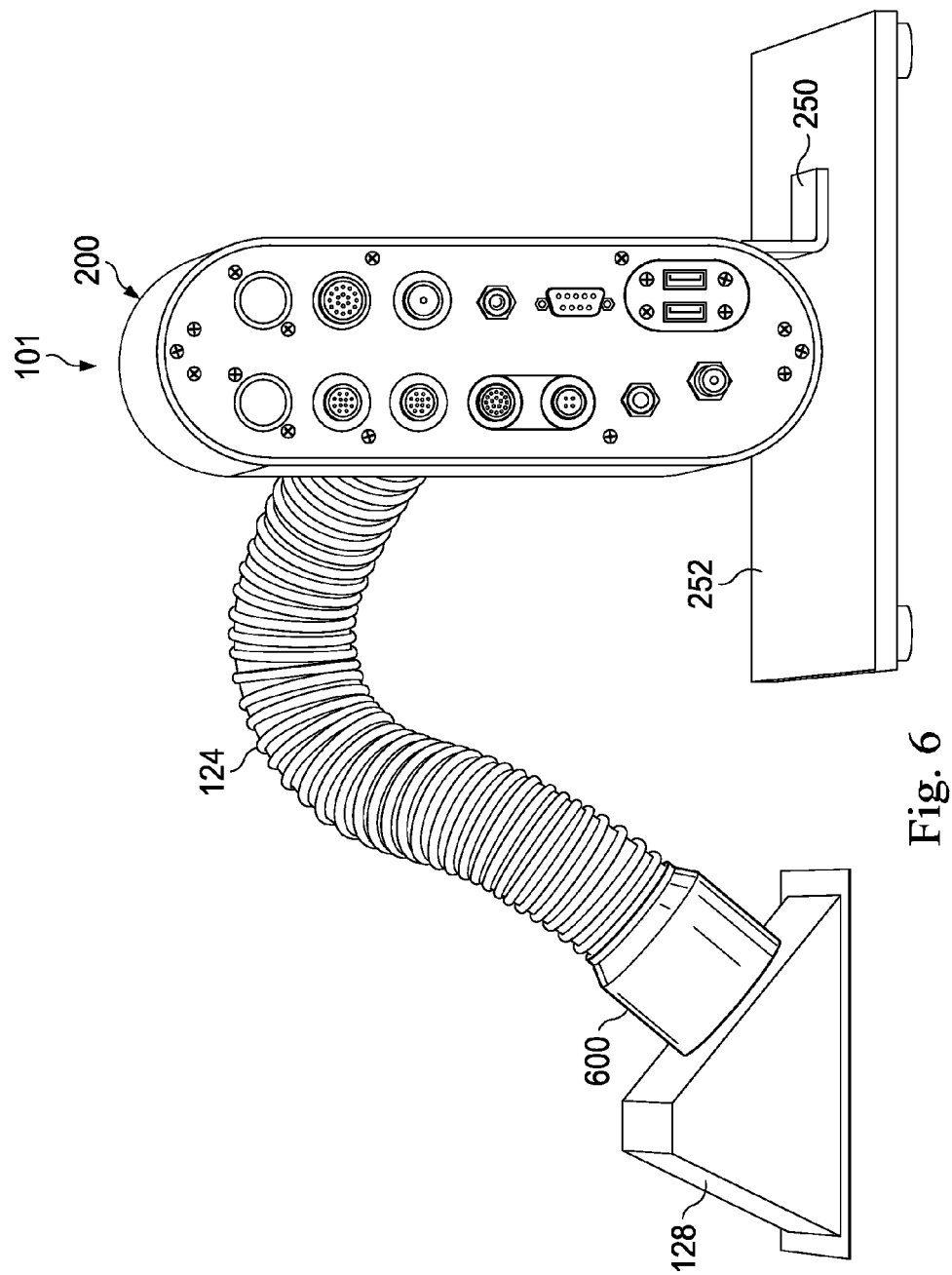
FIG. 6 is a diagrammatic front perspective view of an aspect of a medical communication system installed in a medical environment.

FIG. 6 is a diagrammatic front perspective view of an aspect of the medical communication system 100 installed in a medical environment. Specifically, the hub 101 is mounted to the floor stand 252 and flexible protective hose 124 extends from the rear panel 212 to a straight coupler 600 which is coupled to the trench entry port 128. In some embodiments, the trench entry port 128 includes a second aperture (not shown) disposed on the side opposite of the straight coupler 600. This second aperture may be used to pass additional cables from the catheter lab into the trench below.

Figure 8:
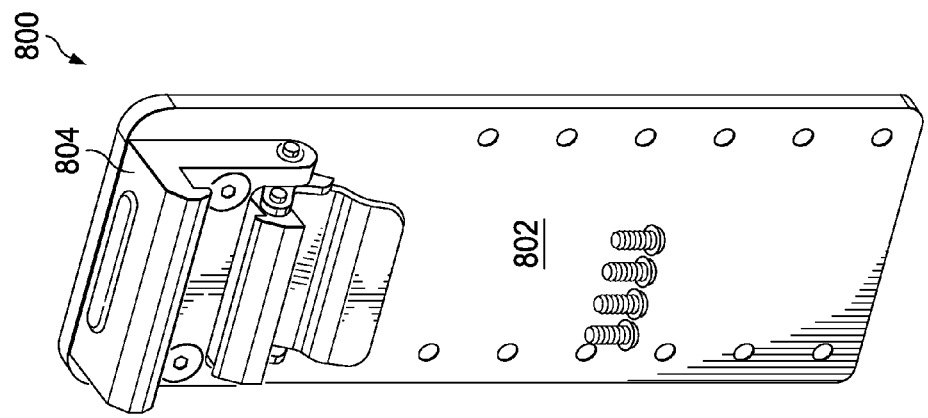
FIG. 8 is a diagrammatic perspective view of a vertical rail mount.
Figure 7:
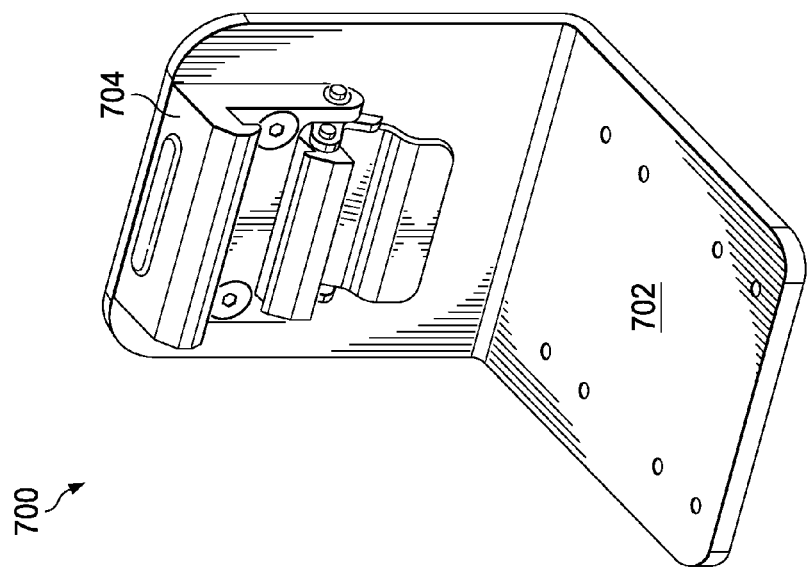
FIG. 7 is a diagrammatic perspective view of a horizontal rail mount.

With reference now to FIGS. 7-10, illustrated are four mounting brackets that may be coupled to the hub 101 so that the hub may be dynamically mounted in a medical environment such as catheter lab 102. FIG. 7 is a diagrammatic perspective view of a horizontal rail mount 700. The horizontal rail mount 700 includes a mounting surface 702 that is configured to couple to either the bottom mounting surface 202 or the top mounting surface 204 on the hub 101. The mounting surface 702 includes a set of mounting apertures that align with either the set of mounting apertures 206 or 208 on the hub 101. In the illustrated embodiment, the set of mounting apertures on the mounting surface 702 conforms to the VESA hole mount pattern, but, alternatively, may be configured to conform to a different pattern depending on the pattern implemented on the mounting surfaces of the hub 101. When the mounting apertures on the mounting surface 702 are aligned with either the set of mounting apertures 206 or 208 on the hub 101, connectors such as screws nay pass through the aligned apertures and releasably couple the horizontal rail mount 700 to the hub 101. The horizontal rail mount 700 further includes a rail clamp 704 that is configured to releasably couple to a rail on or near a patient table in a catheter lab. In the illustrated embodiment, the rail clamp 704 is physically configured to mate with a standardized rail, and when the clamp is so mated, the attached hub 101 will be in a horizontal position. FIG. 8 is a diagrammatic perspective view of a vertical rail mount 800 that is configured to be coupled to the hub 101. Specifically, the vertical rail mount 800 is similar to the horizontal rail mount 700 in that it has a mounting surface 802 with a set of standardized mounting apertures and a rail clamp 804. However, when the hub 101 is coupled to the mounting surface 802 and the rail clamp 804 is clamped to a patient table rail, the hub 101 will be in a vertical position.

Figure 9:
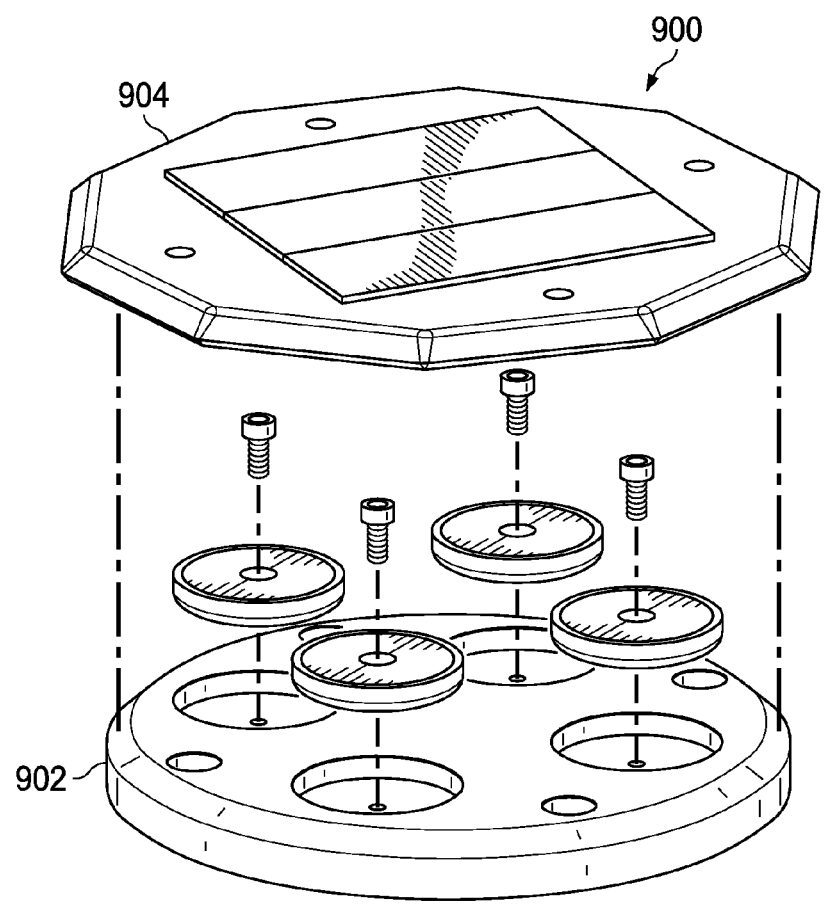
FIG. 9 is a diagrammatic perspective view of a magnetic mounting system.

FIG. 9 is a diagrammatic perspective view of a magnetic mounting system 900 configured to allow the hub 101 to be mounted in a variety of locations around a catheter lab. The mounting system 900 includes a magnetic mount plate 902 with magnets disposed therein. The magnetic mount plate 902 is configured to releasably couple to either the bottom mounting surface 202 or the top mounting surface 204 on the hub 101 via a set of mounting apertures that align with the mounting apertures on the hub. The magnetic mounting system 900 further includes a receiver plate 904 that may be mounted to a wall, floor, ceiling or any other flat surface in a catheter lab. The receiver plate 904 is configured to receive the mount plate 902 and hold it in place via magnetic force.

Figure 10:
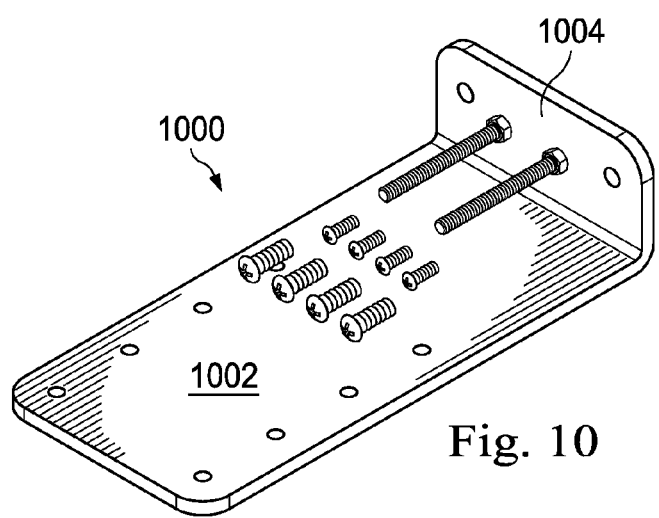
FIG. 10 is a diagrammatic perspective view of an angled mounting bracket.

FIG. 10 is a diagrammatic perspective view of an angled mounting bracket 1000 that is configured to couple to the hub 101. The angled mounting bracket 1000 includes a mounting surface 1002 that is configured to be releasably coupled to either the bottom mounting surface 202 or the top mounting surface 204 on the hub 101 via a set of mounting apertures that align with the mounting aperture on the hub. The angled mounting bracket 1000 further includes an angled surface 1004 configured to fit flush against and releasably couple to a right angled surface in a catheter lab or other medical environment. For instance, the angled mounting bracket 1000 may be affixed to a corner of a gas box disposed under a patient table.

Figure 11A:
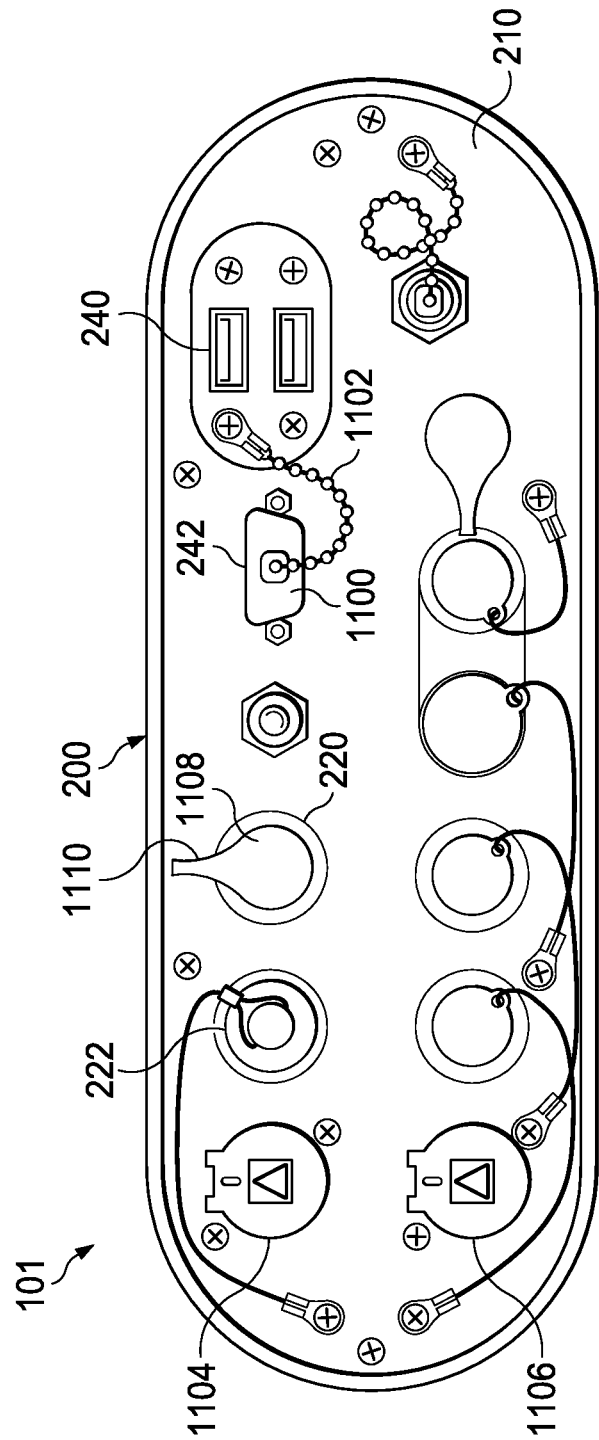
FIG. 11A is a front view of a powered medical communication hub in a fluid-resistant configuration.

FIG. 11A is a front view of the hub 101 in a fluid-resistant configuration. Specifically, as shown in FIG. 11A, a plurality of protective caps are disposed over the connectors on the front panel 210 to prevent fluid or foreign substances from entering the connectors. As mentioned above in association with FIGS. 2A and 2B, many of the connectors on the front panel 210 are sealed to provide some resistance against fluid ingress, but the illustrated caps provide further protection. It is contemplated that the caps shown in FIG. 11A may remain on their respective connectors during a patient procedure if their respective connectors are not in use. In the illustrated embodiment, the caps are commercially available from Souriau SAS, but alternatively, they may be any other type of cap configured to seal the connectors on the hub 101. Each cap is physically configured to mate with a specific connector so that the resulting seal is water-tight. For example, a trapezoid-shaped dust cap 1100 is disposed over the VGA connector 242. The dust cap 1100 includes a lanyard 1102 extending from the dust cap to the front panel 210. As another example, the fiber optic connectors 224 and 226 include flip caps 1104 and 1106 that are mounted to the connectors on hinges. As such, the flip caps 1104 and 1106 may be flipped open when cables need to be connected to the fiber optic connectors 224 and 226, and flipped close when the cables are disconnected. As mentioned above, the USB connectors 240 are sealed and are fluid-resistant, and thus do not require extra protection. As yet another example, in the illustrated embodiment of FIG. 11A, the circular-shaped IVUS PIM connector 220 has a circular-shaped protective cap 1108 disposed thereon. The protective cap 1108 is tethered to the connector 220 via a flexible arm 1110.

Figure 11B:
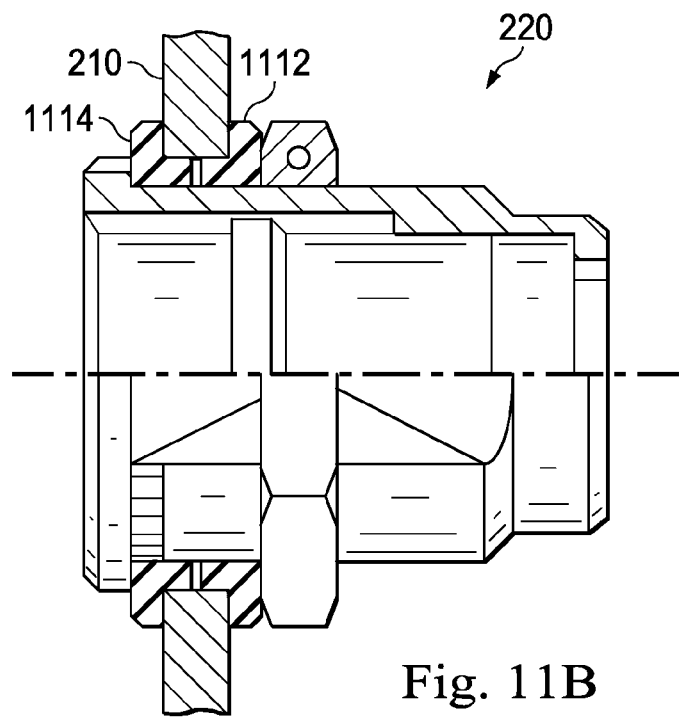
FIG. 11B is a diagrammatic sectional side view of a connector on a front panel of the powered medical communication hub of FIG. 11A.
Figure 11C:
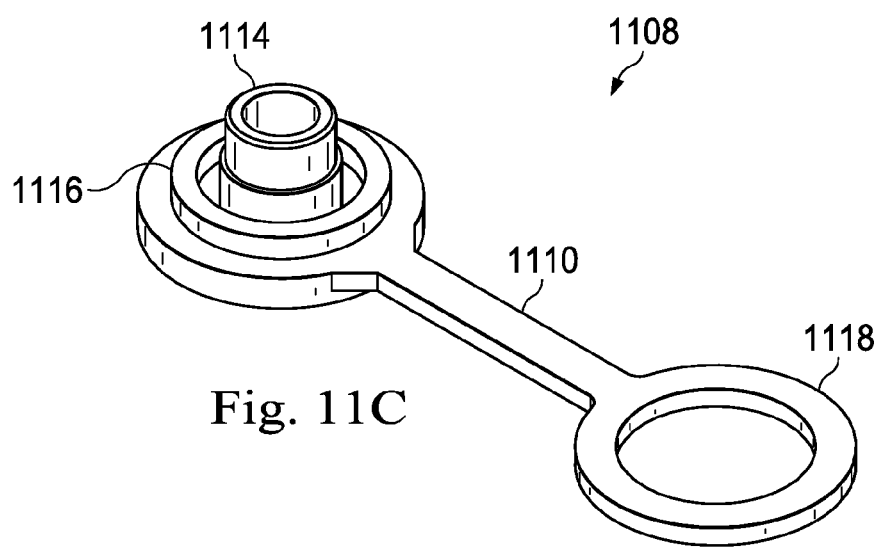
FIG. 11C is a diagrammatic perspective view of a protective cap according to various aspects of the present disclosure.

Referring now to FIGS. 11B and 11C, FIG. 11B is a diagrammatic sectional side view of the IVUS PIM connector 220 on the front panel of the hub 101, and FIG. 11C is a diagrammatic perspective view of the protective cap 1108. As noted above, the interface between the front interface panel 210 and the connector 220 is fluid resistant. This is due in part to a pair of complementary washers 1112 and 1114. The washers 1112 and 1114 are disposed around the connector 220 on either side of the front panel 210 to create a fluid-resistant seal therebetween. As shown in FIG. 11C, the protective cap 1108 is configured to removeably mate with the connector 220 to keep dust, fluid, and other particles out of the connector. The cap 1108 includes an inner ring 1114 and an outer ring 1116 that are configured to create a fluid-resistant seal when engaged with the connector 220. The cap 1108 also includes a retaining portion 1118 configured to fixedly engage an outside portion of the connector 220. When so engaged, the cap 1108 is tethered to the connector 220 via the flexible arm 1110. The cap 1108 is just one example of a protective cap that may be used with the connectors on the hub 101 and other caps may be used that are configured in a different manner, for instance, to mate with connectors with different shapes than the connector 220.

FIG. 12 is a functional block diagram of an embodiment of a powered medical communication hub. As shown in FIG. 2A, the hub 101 may include the IVUS PIM connector 220, the functional measurement (FM) tool connector 222, the first and second fiber optic connector 224 and 226, the OCT PIM connector 228, the bedside control surface connector 230, the FLIVUS PIM connector 232, the FLIVUS footswitch connector 234, the auxiliary power connector 236, the ECG/aortic device connector 238, the USB connectors 240, and the VGA display connector 242. As shown in FIG. 12, the IVIS PIM connector 220 is communicatively coupled to the processing system 120 via a link 1200. A cable 1202 transmitting power, ground, and data signals extends from the processing system 120 to the link 1200, where the signals are internally forwarded to the IVUS PIM connector 220. In some embodiments, the link 1200 and the connector 220 may be integrated such that the cable 1202 running from the processing system 120 to the hub 101 extends through the aperture 214 in the rear panel 212 (FIG. 3) and couples to one side of the connector 220/link 1220, and a cable running from the IVUS PIM 112 to the hub 101 couples to the other side of the connector 220. In other embodiments, however, the link 1200 may be integrated into the rear panel 212 such that the cable 1202 running from the processing system 120 to the hub 101 does not extend into the interior of the hub. The hub 101 further includes a link 1204 that communicatively couples the processing system 120 to the FM tool connector 222. A cable 1206 transmitting power, ground, and data signals extends from the processing system 120 to the link 1204, where the signals are internally forwarded to the FM tool connector 222, which forwards the signals to a connected FM tool, such as a FM Pimette 1207. Similar to the link 1200, the link 1204 may, in some embodiments, be integrated into the FM connector 222 or, alternatively, it may be disposed on the rear panel 212.

The hub 101 further includes a MultiFiber Push-On (MPO) link 1208 to which the first and second fiber optic connectors 224 and 226 are internally coupled. In general, the MPO link 1208 is configured to aggregate fiber optic signals and route them over a single fiber optic line. As shown in FIG. 12, a single fiber optic cable 1210 extends from the processing system 120, through the aperture 212 in the rear panel 214, and to the MPO link 1208 where data destined for the first and second fiber optic connectors 224 and 226 is parsed and routed to the appropriate connector. In some embodiments, the MPO link 1208 may be coupled to a printed circuit assembly (PCA) disposed inside of the hub 101 near the aperture 214, but, in other embodiments, the MPO link may be disposed on the rear panel 212.

The hub 101 includes links 1212 and 1214 that respectively communicatively couple the processing system 120 to the OCT PIM connector 228 and the bedside control surface connector 230. As mentioned above, the connectors 228 and 230 pass Ethernet-based data signals to connected medical-sensing tools. Thus, in the illustrated embodiment, the links 1212 and 1214 are RJ45 jacks that respectively accept Cat 5e cables 1216 and 1218. However, in other embodiments, the links 1212 and 1214 may accept Ethernet-based data over coaxial, fiber optic, or some other type of suitable cable. In some embodiments, the links 1212 and 1214 may be integrated into a PCA disposed within the hub 101 and communicatively coupled to the connectors 228 and 230 via conductive traces on the PCA, but, in other embodiments, the links 1212 and 1214 may be disposed on the rear panel 212 for easy access. The hub 101 further includes a link 1220 configured to communicatively couple the processing system 120 to the ECG device connector 238, and thus the ECG device 116. In some embodiments, the link 1220 may be integrated into the ECG device connector 238 such that a ECG-signal cable 1222 running from the processing system 120 to the hub 101 extends through the aperture 214 in the rear panel 212 and couples to one side of the connector 238/link 1220, and a cable running from the ECG device 116 to the hub 101 couples to the other side of the connector 238. But, in other embodiments, the link 1220 may be disposed on the rear panel 212 such that the cable 1222 running from the processing system 120 to the hub 101 does not extend into the interior of the hub. Additionally, the hub 101 includes a link 1224 configured to communicatively couple the processing system 120 to the VGA connector 242 and pass video information to the display 122. In the illustrated embodiment, the link 1224 accepts a male VGA connector disposed on the end of a cable 1226 coupled to the workstation 120. However, in other embodiments, the link 1224 may be configured to accept other video-based connectors such as a DVI connector, an HDMI connector, a DisplayPort connector, or an S-Video connector. Similar to the links 1200, 1204, and 1220, the link 1224 may, in some embodiments, be integrated into the its associated connector 242 or, alternatively, it may be disposed on the rear panel 212 for easy access.

The hub 101 further includes a link 1228 and a wireless communication module 1230 that is operable to communicate with medical sensing-related tools in close proximity to the hub, such as a wireless-ready PIM. In one embodiment, the wireless communication module 1230 may be a wireless personal area network (WPAN) communication module such as an Ultra-wide band (UWB) module, a wireless FireWire module, or wireless USB module, a Bluetooth module, a IEEE 802.11-based wireless module or some other high-speed wireless module. In the illustrated embodiment, data passes over a data cable 1232 to link 1228, which forwards it to the wireless communication module 1230 to be wirelessly transmitted. In some embodiments, the link 1228 may be a RJ45 connector through which Ethernet-based data passes, but in other embodiments it may be another type of connector through which Ethernet-based data may pass or may transmit a different type of data. As with the links 1212 and 1214, the link 1228 may be integrated into a PCA disposed inside of the hub 101 in some embodiments or it may be disposed on the rear panel 212 in other embodiments.

Further, the hub 101 includes a remote extender 1234. In general, the remote extender 1234 is configured to extend the range of USB communications by converting USB-based data to fiber optic-based data so that the data may be transported over long distances (e.g. up to 500 meters). In the illustrated embodiment, the USB connectors 240 are communicatively coupled to the remote extender 1234, which is in turn, coupled to the MPO link 1208. As such, the processing system 120 may communicate with USB-based devices such an input device 1236 (e.g. joystick, mouse, keyboard, touchpad etc) even if the hub 101 is located hundreds of meters from the workstation. Additionally, the FLIUVS PIM connector 232 is communicatively coupled to the remote extender 1234, and thus may pass USB-based data to the processing system 120 via the hub 101. Further, as shown in FIG. 12, the FLIVUS foot switch connector 234 and the ECG device connector 238 are communicatively coupled to the FLIVUS connector 232 so that signals from a FLIVUS footswitch 1238 and the ECG device 116 may be used to coordinate data collection by a FLIVUS PIM 1240 coupled to the connector 232.

The hub 101 includes a power distribution module 1242 configured to distribute power to medical sensing-related tools connected to the hub. In the illustrated embodiment, the power distribution module 1242 is a hardware-based module. However, in other embodiments, the module 1242 may be a combination of hardware and software, in which software controls power flow through the hardware. In the illustrated embodiment, a link 1244 electrically couples the power distribution module 1242 to a 48 volt DC medicalgrade power supply in the workstation 120. In other embodiments, however, the power distribution module 1242 may draw power from another power source such as a wall receptacle. The power distribution module 1242 converts the power provided by the processing system 120 into a plurality of power amounts (i.e. levels), which are appropriately routed to various connectors in the hub 101. For instance, the power distribution module 1242 is electrically coupled to the first and second fiber optic connectors 224 and 226 and provides them with 48 volts DC. The power distribution module 1242 is also electrically coupled to the OCT PIM connector 228, the bedside control surface connector 230, the auxiliary power connector 236, and the FLIVUS PIM connector 232 and respectively provides them with, 48 volts DC, 12 volts DC, 24 volts DC, and 48 volts DC. Additionally, the power distribution module 1242 provides 12 volts DC to the wireless module and 5 volts DC to the remote extender 1234 which, in turn, supplies the USB connectors 240 with 5 volts DC. In alternative embodiments, the power amounts distributed to the connectors may vary. In further embodiments, the power distribution module 1242 may be operable to determine the amount of power required by medical sensing-related tool connected to a connector on the hub 101 and dynamically supply the correct amount of power. In yet further embodiments, the hub 101 may include a controller to interrogate newly-connected medical sensing tools to determine operational attributes such as voltage requirements. U.S. Patent Application No. 61/473,625, entitled "MEDICAL SENSING COMMUNICATION SYSTEM AND METHOD", discloses a medical sensing communication system that includes a controller and power supply unit that are operable to dynamically supply different medical sensing tools with different amounts of power based on their needs and is hereby incorporated by reference in its entirety. In the illustrated embodiment, the processing system 120 provides the hub 101 with 48 volts DC via a power cable 1246 that is coupled to the link 1244. In some embodiments, the link 1244 may be coupled to a PCA disposed inside of the hub 101 near the aperture 214, but, in other embodiments, the link 1244 may be disposed on the rear panel 212 for easy access. Additionally, as shown in FIG. 12, the hub 101 may be electrically coupled to a ground line 1248 via a cable 1250. Although not shown for purposes of clarity, the ground is distributed to the various connectors on the front panel of the hub 101 that draw power from the power distribution module 1242 so that the connectors may pass along the ground to the connected tools.

As mentioned above, the front interface panel 210 (FIG. 2A) and the connectors 220, 222, 224, 226, 228, 230, 232, 234, 236, 238, 240, and 242 described above may together be considered a forward interface assembly. Further, the rear interface panel 212 (FIG. 3) and the links 1200, 1204, 1208, 1212, 1214, 1220, 1224, 1228, and 1244 may together considered a rear interface assembly. Thus, as described above, in some embodiments the rear interface assembly may include internal portions of the hub 101 (e.g. when the links are integrated into a PCA disposed inside of the hub).

With reference now to FIGS. 1, 3 and 12, the rear interface assembly of the hub 101 may be assembled in the following manner. First, after cables 1202, 1206, 1216, 1218, 1246, 1222, 1210, 1232, 1226, and 1250 have been installed in trench 126 such that they enter the catheter lab 102 through trench entry port 128, they may be threaded through a coupler, the flexible hose 124, and another coupler such as straight coupler 262. With the rear panel 212 and/or housing removed from the hub 101, the cables may then be threaded through the aperture 214 in the rear panel 212 and coupled to their respective links inside of the hub 101. For instance, the cables 1216 and 1218 may be coupled to the links 1212 and 1214, which, in some embodiments, may be integrated into a PCA disposed within the hub 101. Once every cable extending from the processing system 120 has been coupled to the hub 101, the rear panel 212 may be fixedly secured to the hub 101 with connectors such as screws. As noted above, when the rear panel 212 is coupled to the hub 101, the gasket 213 creates a fluid-resistant interface between the two. Next, the coupler 262 may be fixedly coupled around the aperture 214 in the rear panel 212 with connectors such as screws, and the flexible tube 124 may be fixedly secured to coupler 262 on its hub-end and to another coupler on its trench-end. Once assembly is complete, the cables connecting the processing system 120 to the hub 101 and their associated links inside of the hub are protected from damaging elements in the catheter lab such as fluids and impact. One of ordinary skill in the art would understand that the previous assembly scenario is simply one example and other scenarios using different elements and/or positioning may be implemented.

Figure 13:
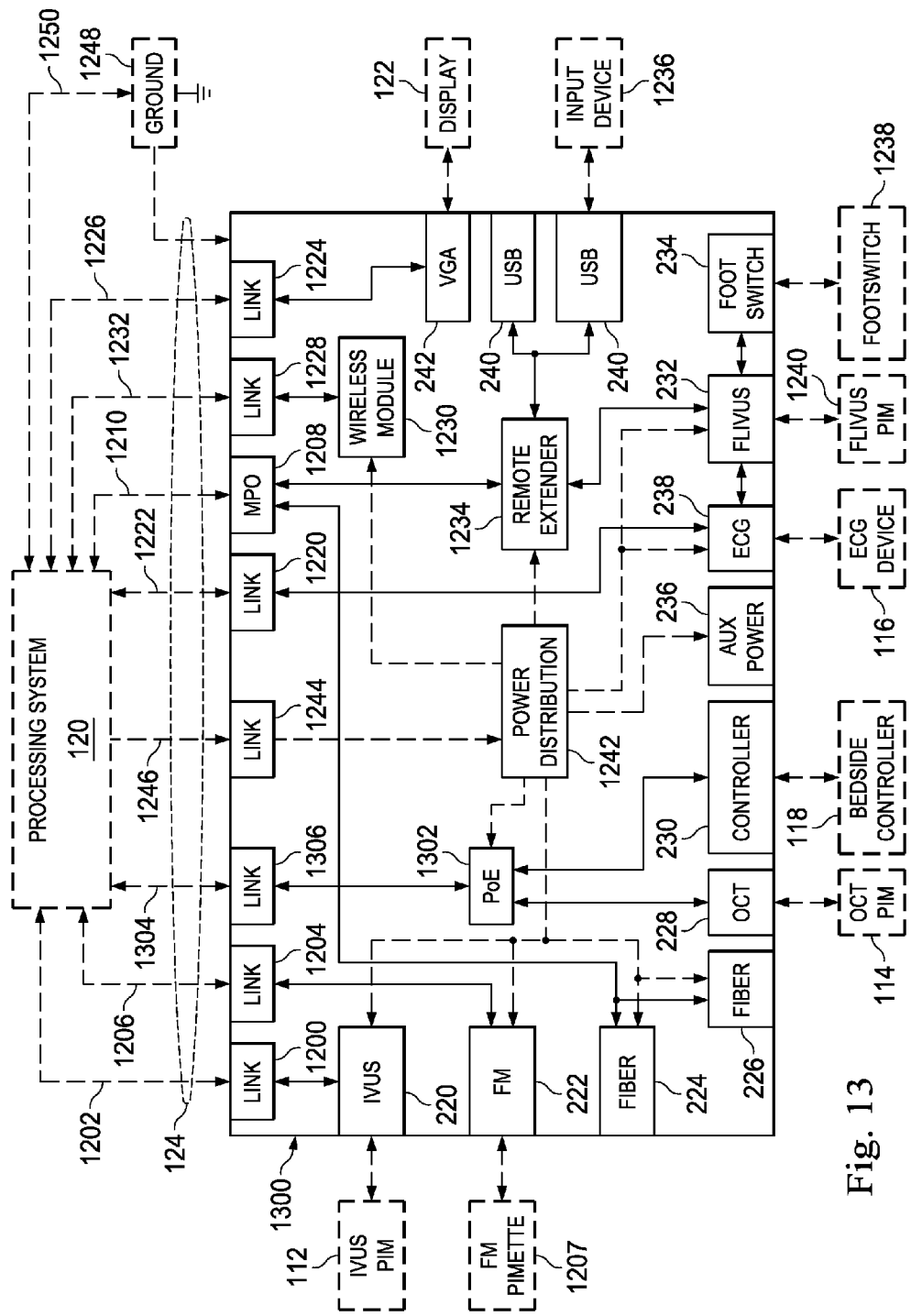
FIG. 13 is a functional block diagram of a further embodiment of a powered medical communication hub.

FIG. 13 is a functional block diagram of a powered medical communication hub 1300 according to another embodiment of the present invention. The hub 1300 is similar to the hub 101 shown in FIG. 12 but differs in several aspects as described below. Specifically, the hub 1300 includes a Power-over-Ethernet (PoE) module 1302 communicatively interposed between the processing system 120 and the OCT PIM connector 228 and the bedside control surface connector 230. A shown in FIG. 13, a single Cat5e cable 1304 (or other Ethernet-compatible communication medium) may extend from the processing system 120 to an Ethernet-based link 1306 in the hub 1300. The link 1306, in turn, communicatively couples to the PoE module 1302, where packetized data is routed to the appropriate connector. Further, the PoE module 1302 draws power (e.g. 48 volts DC) from the power distribution module 1242 and passes it to downstream Ethernet-based devices via the connectors 228 and 230. The downstream devices may, in turn, utilize the power as needed. In alternative embodiments, the PoE module 1302 may draw power from the processing system 120 via link 1306 in addition to or instead of drawing power from the power distribution system 1242. Further, in the embodiment of FIG. 12, the IVUS PIM connector 220 and FM tool connector 222 draw power directly from their respective links 1200 and 1204, however, in the embodiment of FIG. 13, these connectors may draw power directly from the power distribution module 1242. Additionally, in hub 1300, the ECG connector 238 may draw power from the power distribution module 1242 as well.

Figure 14:
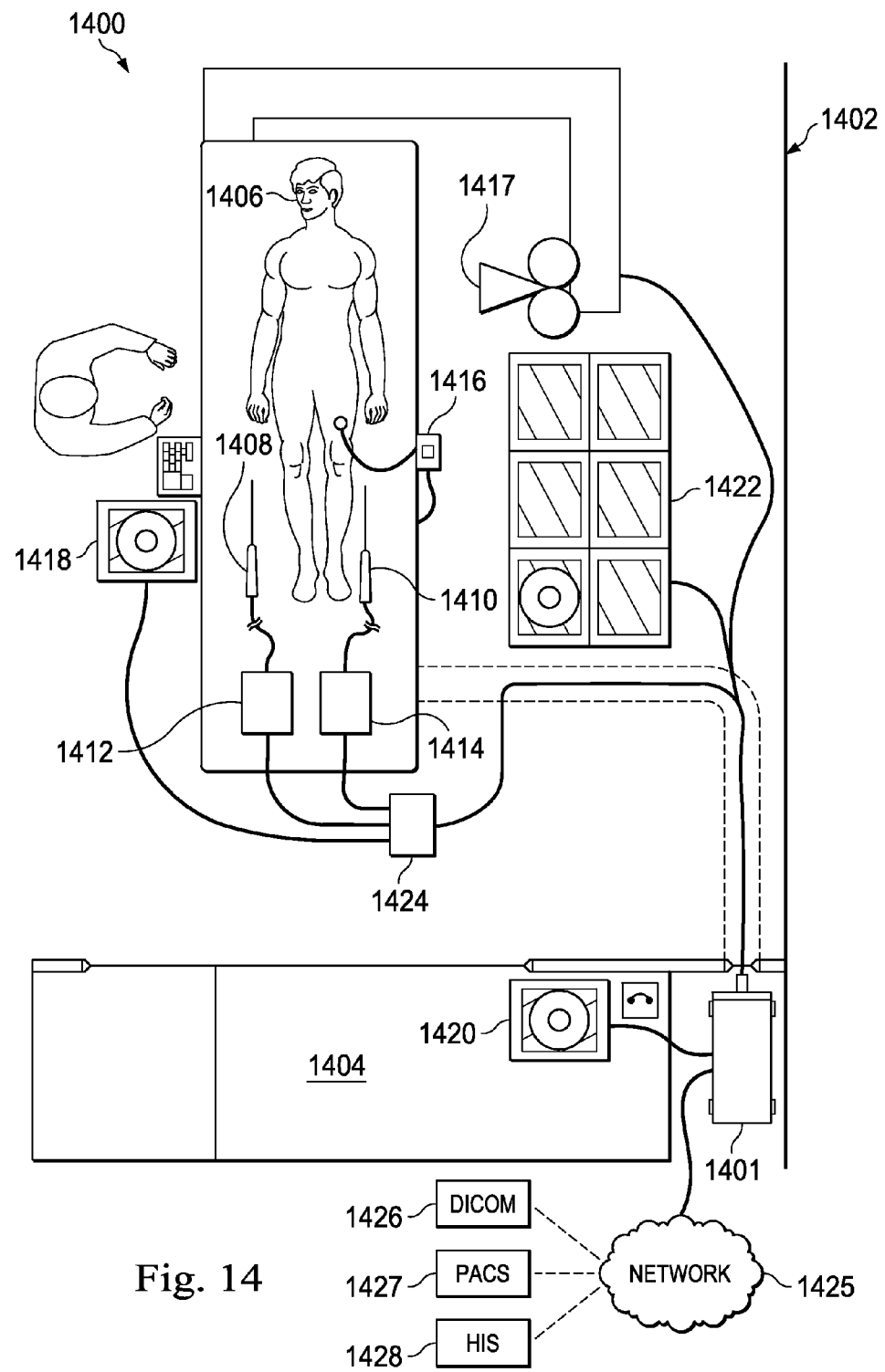
FIG. 14 is a schematic drawing depicting a medical sensing system including a multi-modality processing system according to one embodiment of the present disclosure.

FIG. 14 is a schematic drawing depicting a medical sensing system 1400 including a multi-modality processing system 1401 according to one embodiment of the present disclosure. In general, the medical sensing system 1400 provides for coherent integration and consolidation of multiple forms of acquisition and processing elements designed to be sensitive to a variety of methods used to acquire and interpret human biological physiology and morphological information. More specifically, in system 1400, the multi-modality processing system 1401 is an integrated device for the acquisition, control, interpretation, and display of multi-modality medical sensing data. In one embodiment, the processing system 1401 is a computer workstation with the hardware and software to acquire, process, and display multi-modality medical sensing data, but in other embodiments, the processing system 1401 may be any other type of computing system operable to process medical sensing data.

In the embodiments in which processing system 1401 is a computer workstation, the system includes at least a processor such as a microcontroller or a dedicated central processing unit (CPU), a non-transitory computer-readable storage medium such as a hard drive, random access memory (RAM), and/or compact disk read only memory (CD-ROM), a video controller such as a graphics processing unit (GPU), and a network communication device such as an Ethernet controller.

In the illustrated embodiment, the medical sensing system 1400 is deployed in a catheter lab 1402 having a control room 1404, with the processing system 1401 being located in the control room. In other embodiments, the processing system 1401 may be located elsewhere, such as in the catheter lab 1402 itself as will be described in association with FIGS. 18 and 19. The catheter lab 1402 includes a sterile field but its associated control room 1404 may or may not be sterile depending on the requirements of a procedure and/or health care facility. The catheter lab and control room may be used to perform on a patient any number of medical sensing procedures such as angiography, intravascular ultrasound (IVUS), virtual histology (VH), forward looking IVUS (FL-IVUS), intravascular photoacoustic (IVPA) imaging, a fractional flow reserve (FFR) determination, a coronary flow reserve (CFR) determination, optical coherence tomography (OCT), computed tomography, intracardiac echocardiography (ICE), forward-looking ICE (FLICE), intravascular palpography, transesophageal ultrasound, or any other medical sensing modalities known in the art. For example, in catheter lab 1402 a patient 1406 may be undergoing a multi-modality procedure either as a single procedure or in combination with one or more sensing procedures, in which IVUS data will be collected with an IVUS catheter 1408 and OCT data will be collected with an OCT catheter 1410. The IVUS catheter 1408 may include one or more sensors such as a phased-array transducer. In some embodiments, the IVUS catheter 1408 may be capable of multi-modality sensing such as IVUS and IVPA sensing. The OCT catheter 1410 may include one or more optical sensors.

In the embodiment illustrated in FIG. 14, the medical sensing system 1400 includes a number of interconnected medical sensing-related tools in the catheter lab 1402 and control room 1404 to facilitate this multi-modality workflow procedure, including an IVUS patient isolation module (PIM) 1412, an OCT PIM 1414, an electrocardiogram (ECG) device 1416, an angiogram system 1417, a bedside control surface 1418, a control room control surface 1420, and a boom display 1422. A bedside utility box (BUB) 1424 in the catheter lab 1402 acts as a hub for the PIMs 1412 and 1414, ECG device 1416, and bedside control surface 1418 and communicatively couples them to the processing system 1401. In the illustrated embodiment, the angiography system 1417, control room control surface 1420, and boom display 1422 are communicatively coupled directly to the processing system 1401. However, in alternative embodiments, these tools may be coupled to the processing system 1401 via the BUB 1424. In one embodiment, the BUB 1424 is a passive cable pass-through device that consolidates wires and feeds them into an under-floor cabling trench, but, alternatively, in other embodiments, the BUB 1424 may contain logic and communication circuitry to actively coordinate communication between the medical sensing tools and the processing system 1401. U.S. Provisional Patent Application No. 61/473,625, entitled "MEDICAL SENSING COMMUNICATION SYSTEM AND METHOD" and filed on Apr. 8, 2011, discloses a bedside utility box that intelligently couples medical sensing-related tools and is hereby incorporated by reference in its entirety. Further, the multi-modality processing system 1401 is communicatively coupled to a data network 1425. In the illustrated embodiment, the data network 1425 is a TCP/IP-based local area network (LAN), however in other embodiments, it may utilize a different protocol such as Synchronous Optical Networking (SONET), or may be a wide area network (WAN). The processing system 1401 may connect to various resources via the network 1425. For example, the processing system 1401 may communicate with a Digital Imaging and Communications in Medicine (DICOM) system 1426, a Picture Archiving and Communication System (PACS) 1427, and a Hospital Information System 1428 through the network 1425.

Additionally, in the illustrated embodiment, medical sensing tools in system 1400 are communicatively coupled to the processing system 1401 via a wired connection such as a standard copper link or a fiber optic link, but, in alternative embodiments, the tools may be connected to the processing system 1401 via wireless connections using IEEE 802.11 Wi-Fi standards, Ultra Wide-Band (UWB) standards, wireless FireWire, wireless USB, or another high-speed wireless networking standard.

In the medical sensing system 1400, the IVUS PIM 1412 and OCT PIM 1414 are operable to respectively receive medical sensing data collected from the patient 1406 by the IVUS catheter 1408 and OCT catheter 1410 and are operable to transmit the received data to the processing system 1401 in the control room 1404. In one embodiment, the IVUS PIM 1412 and OCT PIM 1414 transmit the medical sensing data over a Peripheral Component Interconnect Express (PCIe) data bus connection, but, in other embodiments, they may transmit data over a USB connection, a Thunderbolt connection, a FireWire connection, or some other high-speed data bus connection. In one embodiment, the PIMs 1412 and 1414 include analog to digital (A/D) converters and transmit digital data to the processing system 1401, however, in other embodiments, the PIMs transmit analog data to the processing system. Additionally, the ECG device 1416 is operable to transmit electrocardiogram signals or other hemodynamic data from patient 1406 to the processing system 1401. In some embodiments, the processing system 1401 may be operable to synchronize data collection with the catheters 1408 and 1410 using ECG signals from the ECG 1416. Further, the angiogram system 1417 is operable to collect x-ray, computed tomography (CT), or magnetic resonance images (MRI) of the patient 1406 and transmit them to the processing system 1401. In one embodiment, the angiogram system 1417 may be communicatively coupled to the processing system 1401 through the network 1425, but, in other embodiments, the angiogram system may be more directly coupled to the processing system 1401, for example through an adapter device. Such an adaptor device may transform data from a proprietary third-party format into a format usable by the processing system 1401. In some embodiments, the processing system 1401 may co-register image data from angiogram system 1417 (e.g. x-ray data, MRI data, CT data, etc.) with sensing data from the IVUS and OCT catheters 1408 and 1410. As one aspect of this, the co-registration may be performed to generate three-dimensional images with the sensing data.

The bedside control surface 1418 is also communicatively coupled to the processing system 1401 via the BUB 1424 and provides user control of the particular medical sensing modality (or modalities) being used to diagnose the patient 1406. In the current embodiment, the bedside control surface 1418 is a touch screen that provides user controls and diagnostic images on a single surface. In alternative embodiments, however, the bedside control surface 1418 may include both a non-interactive display and separate controls such as physical buttons and/or a joystick. In the integrated medical sensing system 1400, the bedside control surface 1418 is operable to present workflow control options and patient image data in graphical user interfaces (GUIs). The bedside control surface 1418 is capable of displaying GUIs for multiple modalities, and thus a clinician does not have to physically move between user interface devices when switching sensing modalities.

The control room control surface 1420 in the control room 1404 is also communicatively coupled to the processing system 1401 and, as shown in FIG. 14, is adjacent to catheter lab 1402. In the current embodiment, the control room control surface 1420 is similar to the bedside control surface 1418 in that it includes a touch screen and is operable to display multitude of GUI-based workflows corresponding to different medical sensing modalities. In some embodiments, the control room control surface 1420 may be used to simultaneously carry out a different aspect of a procedure's workflow than the bedside control surface 1418. In alternative embodiments, the control room control surface 1420 may include a non-interactive display and standalone controls such as a mouse and keyboard.

The system 1400 further includes the boom display 1422 communicatively coupled to the processing system 1401. The boom display 1422 may include an array of monitors, each capable of displaying different information associated with a medical sensing procedure. For example, during an IVUS procedure, one monitor in the boom display 1422 may display a tomographic view and one monitor may display a sagittal view.

Figure 15:
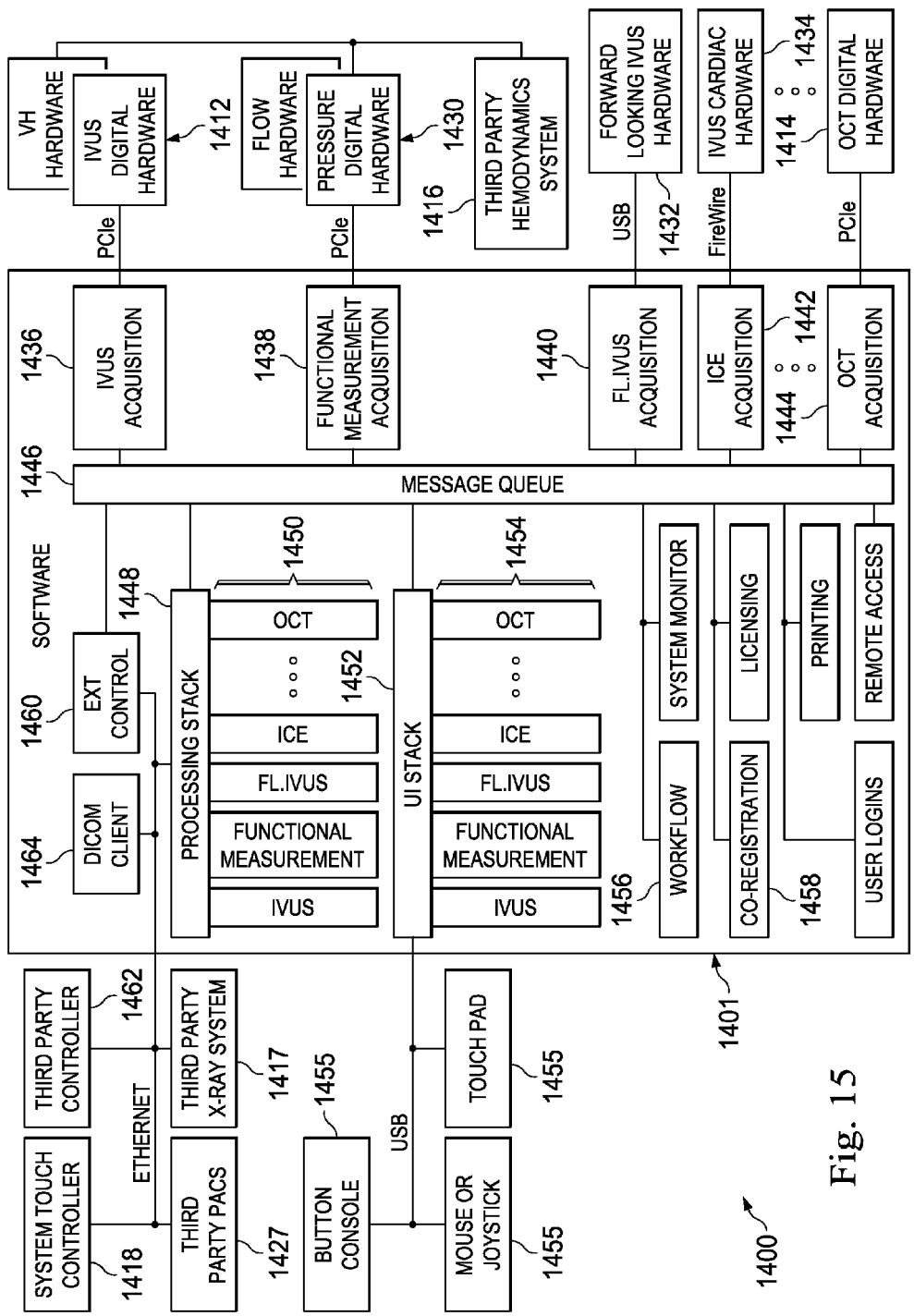
FIG. 15 is a functional block diagram of a software framework executing on an embodiment of the multi-modality processing system in the medical sensing system.

With reference now to FIG. 15, illustrated is a functional block diagram of the software framework executing on an embodiment of the multi-modality processing system 1401 in the medical sensing system 1400. In general, the software framework of processing system 1401 is modular and extensible. That is, the software framework is driven by independent software modules respectively associated with a specific medical sensing modality. This modular design allows the framework to be extended to accommodate additional medical sending modalities without an impact on existing functionality. Further, an internal messaging system facilitates independent data communication between software modules in the framework.

In more detail, in the embodiment shown in FIG. 15, the processing system 1401 is communicatively coupled and operable to receive medical sensing data from a plurality of medical sensing devices. For example, the IVUS PIM 1412, the OCT PIM 1414, the ECG system 1416, and a fractional flow reserve (FFR) PIM 1430 are communicatively coupled to the system 1401 via a PCIe connection. Additionally, a FLIVUS PIM 1432 is communicatively coupled to the system 1401 via a USB connection and a ICE PIM 1434 is communicatively coupled to the system 1401 via a FireWire connection. In other embodiments, additional and/or different medical sensing devices may be coupled to the processing system 1401 via additional and/or different data communication connections known in the art. As mentioned above, some PIMs may send analog medical sensing data to the processing system 1401. In such a case, medical sensing data may be digitized as it arrives, for example, by the PCIe hardware onboard the system 1401.

To facilitate communication between the processing system 1401 and the medical sensing devices coupled thereto, the software framework includes a plurality of data acquisition modules, each associated with a respective modality (i.e. medical sensing device). For example, an IVUS acquisition module 1436 is operable to receive IVUS data from the IVUS PIM 1412 via the PCIe bus. Likewise, a FFR acquisition module 1438 is operable to receive FFR data from the FFR PIM 1430 via the PCIe bus, a FLIVUS acquisition module 1440 is operable to receive FLIVUS data from the FLIVUS PIM 1432 via the USB bus, an ICE acquisition module 1442 is operable to receive ICE data from the ICE PIM 1434 via the FireWire bus, and an OCT acquisition module 1444 is operable to receive OCT data from the OCT PIM 1414 via the PCIe bus. Once the acquisition modules 1436, 1438, 1440, 1442, and 1444 have received data from the connected medical sensing devices, the modules packetize the data to facilitate intersystem communication. Specifically, the modules are operable to create a plurality of messages from the incoming digital data stream, where each message contains a portion of the digitized medical sensing data and a header. The message header contains information associated with the medical sensing data contained within the message. The format of these messages will be described in more detail in association with FIG. 16. Further, in some embodiments, the acquisition modules 1436, 1438, 1440, 1442, and 1444 may be operable to manipulate the digitized medical sensing data in some way before it is packetized. For example, the acquisition modules may compress the sensing data to make intersystem communication more efficient, or normalize, scale or otherwise filter the data to aid later processing of the data. In some embodiments, this manipulation may be modality-specific. For example, the OCT acquisition module 1444 may identify and discard redundant OCT data before it is packetized to save processing time down the line. The acquisition modules 1436, 1438, 1440, 1442, and 1444 may additionally perform a number of tasks related to the acquisition of data including responding to interrupts generated by the data buses (e.g. PCIe, USB), detecting which medical sensing devices are connected to processing system 1401, retrieving information about connected medical sensing devices, storing sensing device-specific data, and allocating resources to the data buses. In accordance with the modular architecture of the software framework, the data acquisition modules are independent from each other and may be installed or removed without disrupting data acquisition by other modules. Additionally, acquisition modules are independent of the underlying data bus software layers (e.g. through the use of Application Programming Interfaces (APIs)) and thus may be written by third parties to acquire data from third party medical sensing devices.

The software framework further includes a message queue 1446 to facilitate intersystem communication between different components in the processing system 1401. The message queue 1446 is operable to receive messages from software modules within the framework of system 1401, temporarily store the messages, and make the messages available for retrieval by software modules within the framework. For instance, after the acquisition modules 1436, 1438, 1440, 1442, and 1444 packetize incoming medical sensing data into messages, they pass the messages to the message queue 1446, where they wait for further processing. In one embodiment, the message queue 1446 includes modality-specific queues for messages associated with each sensing modality. For example, in such a scenario, a portion of the message queue 1446 may be allocated for messages containing IVUS data received from the IVUS data acquisition module 1436. Further, in some embodiments, the message queue 1446 is operable to make received messages available in a First-In-First-Out (FIFO) manner, wherein messages that arrive on the bus first will be removed from the bus first. In alternative embodiments, the message queue 1446 may make messages available in a different manner for instance by a priority value stored in the message header. In one embodiment, the message queue 1446 is implemented in random-access memory (RAM) in the processing system 1401, but, in other embodiments, the message queue may be implemented in non-volatile RAM (NVRAM), secondary storage (e.g. magnetic hard drives, flash memory, etc), or network-based storage. Further, in one embodiment, messages stored on the message queue 1446 may be accessed by software and hardware modules in processing system 1401 using Direct Memory Access (DMA).

The software framework of processing system 1401 further includes a processing software stack 1448 that supports a layer of processing plug-ins (or modules) 1450. In general, each processing plug-in in the layer 1450 corresponds to a medical sensing modality and processes data associated with that particular sensing modality. For example, an IVUS processing plug-in in layer 1450 may interpret IVUS data received from the IVUS PIM 1412 and convert the data into displayable IVUS images. In one embodiment, the software stack 1448 may expose a set of application programming interfaces (APIs) with which the plug-ins in the layer 1450 may call to access system resources such as the message queue 1446, computational resources, and communication resources. Further, in some embodiments, the plug-in layer 1450 may include co-registration plug-ins, in which medical sensing data from a plurality of medical sensing devices are interpreted and co-registered. To support such co-registration applications, in one embodiment, the software stack 1448 may expose time synchronization APIs for use by the plug-ins and may expose APIs through which the processing modules may access specialized co-registration modules, databases containing co-registration data, or sensing systems producing real-time data for use in co-registration, such as angiography system 1417 or an MRI system.

The processing plug-ins in the layer 1450 are operable to retrieve messages on the message queue 1446 that contain unprocessed medical sensing data. For example, using one or more APIs, a plug-in associated with a sensing modality may query the message queue 1446 to determine if messages corresponding to the sensing modality are waiting to be processed on the bus. If so, the plug-in may retrieve one or more of the oldest messages (in those embodiments using FIFO) and process the raw data therein. After processing the data, the plug-in may re-packetize the data and place a message containing the processed data back on the message queue 1446. In some embodiments, before sending the message to the bus, the plug-ins may insert a flag in the header indicating that the message contains processed data. In other embodiments, however, rather than insert a flag, the plug-in may instead place the messages in a queue in the message queue 1446 that is allocated for messages containing processed data, or perform some other operation to indicate that the medical sensing data in the messages has been processed. Additionally, in some embodiments, after processing medical sensing data, the plug-ins may transmit the processed data to archival systems such as a locally attached mass storage device or the network-based PACS server 1427.

In accordance with the modular architecture of the software framework, the processing plug-ins in the layer 1450 are independent of each other and the software stack 1448 and may be installed or removed without disrupting other plug-ins, and may be written by third parties. Further, they are operable to process signaling and imaging data from multiple medical sensing devices concurrently. In this regard, in some embodiments, the processing software stack 1448 may intelligently make use of the computing resources by identifying generic computing tasks common to concurrently executing processing plug-ins. For example, the processing software stack 1448 may determine that two processing plug-ins (associated with different modalities) each need to perform filtering, image processing, and scan conversion processes on incoming sensing data. Once these common tasks are identified, the software stack 1448 may utilize a library of parallel algorithms to process these tasks concurrently.

The software framework of processing system 1401 further includes a user interface software stack 1452 that supports a layer of graphical user interface (GUI) plug-ins (or modules) 1454. In general, each GUI plug-in in the layer 1454 corresponds to a medical sensing modality and is operable to render a user interface for control of the associated acquisition workflow and display of processed sensing data. In one embodiment, the user interface software stack 1452 may expose APIs with which the plug-ins in the plug-in layer 1454 may call to access system resources such as the message queue 1446, a look-and-feel toolbox, and error handling resources. The look-and-feel toolbox APIs enable the GUI plug-ins to present a standardized user interface with common buttons, parallel workflow formats, and data presentation schemes. In this manner, clinicians may more easily transition between acquisition modalities without additional user interface training. Further, co-registration GUI plug-ins in layer 1454 may present and/or combine processed image or signaling data from multiple modalities. For instance, a GUI plug-in may display an electrocardiogram (ECG) wave adjacent to IVUS imaging data or may display an IVUS image overlaid with borders that were previously drawn on an OCT image. Further, in some embodiments, the UI software stack 1452 may include a multi-tasking framework to coordinate concurrently executing GUI plug-ins. For instance, in the event the processing system 1401 is simultaneously acquiring data associated with more than one modality, the UI software stack may present the user with a modality selector screen on which a desired GUI may be selected.

The GUI plug-ins in layer 1454 are operable to retrieve messages from the message queue 1446 that contain processed medical sensing data. For example, using one or more APIs, a plug-in associated with a sensing modality may query the message queue 1446 to determine if messages associated with the sensing modality are waiting on the bus. If so, the plug-in may retrieve one or more of the oldest messages (in those embodiments using FIFO) and render the processed data therein using the look-and-feel toolbox APIs. The rendered GUI may then be displayed on one or more control/display device such as bedside control surface 1418, control room control surface 1420, and boom display 1422. Further, in some embodiments, additional control devices 1455 (e.g. button consoles, mice, keyboards, touch pads) may be communicatively coupled to the processing system 1401 to facilitate user interaction with the GUIs. In some embodiments, the processing system 1401 may make the rendered GUIs accessible by remote network-connected devices via data network 1425. In this manner, a clinician outside of the catheter lab 1402 may control a data acquisition workflow or passively monitor medical sensing images. Further, in some embodiments, the processing system 1401 may be operable to output independent GUIs to different control devices such that clinicians may perform multiple workflows using the same sensing data simultaneously. Additionally, in accordance with the modular architecture of the software framework, the GUI plug-ins in the layer 1454 are independent of each other and the software stack 1452 and may be installed or removed without disrupting other plug-ins, and may be written by third parties.

The software framework further includes additional software modules to facilitate multi-modality data acquisition and processing. For instance, the processing system includes a workflow module 1456. In general, the workflow module 1456 is operable to set up and coordinate data acquisition workflows for processing system 1401. In some embodiments, the workflow module 1456 may be operable to communicate with the DICOM server 1426 or HIS 1428 via the network 1425 to retrieve patient procedure information, such as scheduling information. Also, the workflow module 1456 may report the sensing capabilities of the processing system 1401 to the DICOM server 1426 or HIS 1428 so that appropriate workflows are assigned to processing system 1401. Further, in some embodiments, the workflow module 1456 may be operable to associate patient information and procedure with messages stored on the message queue 1446. For instance, the module 1456 may retrieve patient information from the DICOM server 1426 and insert the information into the header of messages containing data acquired from the patient before the messages are archived.

Further, the software framework on processing system 1401 includes a co-registration module 1458. In general, the co-registration module 1458 facilitates co-registration of medical sensing data associated with different sensing modalities. For instance, the module 1458 may coordinate the acquisition of data from the angiography system 1417 with the acquisition of data from the IVUS PIM 1412. In some embodiments, the angiography system 1417 may transmit messages containing x-ray imaging data to the message queue 1446, and the co-registration module 1458 may retrieve these messages, extract the data, and co-register it with data extracted from messages placed on the message queue by one of the data acquisition modules 1436, 1438, 1440, 1442, and 1444. Still further, in other embodiments, the co-registration module 1458 may be operable to spatially co-register catheter-gathered data in a two-dimensional or three-dimensional space using previously-generated 2D images or 3D models. For example, a catheter-based sensing tool may include fiducials that are tracked to generate position data during a sensing procedure, and the co-registration module 158 may register this position data against previously acquired MRI data.

Additionally, in other embodiments, the co-registration module 1458 may be operable to facilitate time synchronization among medical sensing devices connected to processing system 1401 for co-registration purposes. For instance, in one embodiment, the co-registration module 1458 may be operable to serve as a master time server for the PIMs 1412, 1430, 1432, 1434, and 1414 using a network-based time synchronization protocol such as the Precision Time Protocol (PTP) or the Network Time Protocol (NTP). In another embodiment, the co-registration module 1458 may be operable to assign a common timestamp to data as it arrives on the message queue 1446 from a plurality of medical sensing devices. Still further, in other embodiments, the processing system 1401 may include a dedicated real-time clock to synchronize sampling by connected medical sensing devices. In such an embodiment, the co-registration module 1458 may utilize the real-time clock to distribute a synchronization signal to connected sensing devices. In some embodiments, the real-time clock may be integrated into the co-registration module 1458. U.S. Provisional Patent Application No. 61/473,591, entitled "DISTRIBUTED MEDICAL SENSING SYSTEM AND METHOD" and filed on Apr. 8, 2011, discloses temporally synchronizing medical sensing data collection in more detail and is hereby incorporated by reference in its entirety.

The software framework on processing system 1401 additionally includes an external controller module 1460 to facilitate communication with a third-party controller 1462. In one embodiment, the controller module 1460 is operable to export control functionality of the processing system 1401 to the third party controller 1462, so that the controller 1462 may present control functions in its user interface. Further, a DICOM client module 1464 in the processing system 1401 may facilitate communication with the DICOM server 1426.

Figure 16:
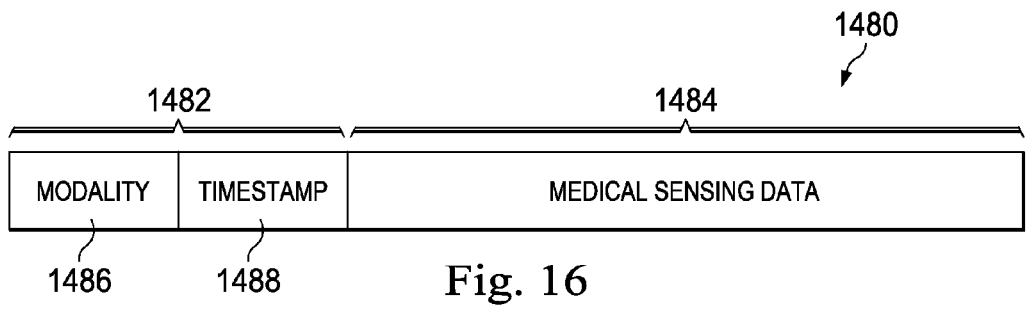
FIG. 16 is an illustration of a message format utilized by the multi-modality processing system in one embodiment of the present disclosure.

With reference now to FIG. 16, illustrated is a message format utilized by the multi-modality processing system 1401 in one embodiment of the present disclosure. As mentioned above, the data acquisition modules 1436, 1438, 1440, 1442, and 1444 may convert incoming medical sensing data into a plurality of messages containing digitized sensing data and associated identifying information. FIG. 16 illustrates an example message 1480. The message 1480 includes a header 1482 and a payload 1484. The payload 1484 includes digitized medical sensing data collected with the medical sensing devices coupled to the processing system 1401. The header 1482 includes information associated with the sensing data in the payload 1484. In the illustrated embodiment, the header 1482 includes blocks 1486 and 1488 that respectively contain modality information associated with the data, and a timestamp. The modality information in block 1486 may include the modality of the data in payload 1484 (e.g. IVUS, OCT, etc.) and, in some embodiments, may also include information about the specific medical sensing device (e.g. catheter, PIM, etc.) with which the data was taken. Further, the timestamp in block 1488 may correspond to the point in time the data in payload 1484 was collected. In some embodiments, the timestamp value may be provided by the originating PIM, but in other embodiments, the timestamp may be provided by the co-registration module 1458, or the data acquisition module responsible for creating the messages. The timestamp (or sequence number) in block 1488 may be used to facilitate temporal co-registration of the sensing data in payload 1484 with data of a different modality. In other embodiments, the header 1482 may include additional information associated with the data in payload 1484 such as procedure date and time, procedure location (e.g. health care facility, catheter lab, etc.), patient identification (e.g. name, social security number, date of birth, etc.), and doctor identification (e.g. name, license number, etc.), analog to digital conversion information, compression information, a flag indicating the processing status of the data, and workflow identification information.

Figure 17:
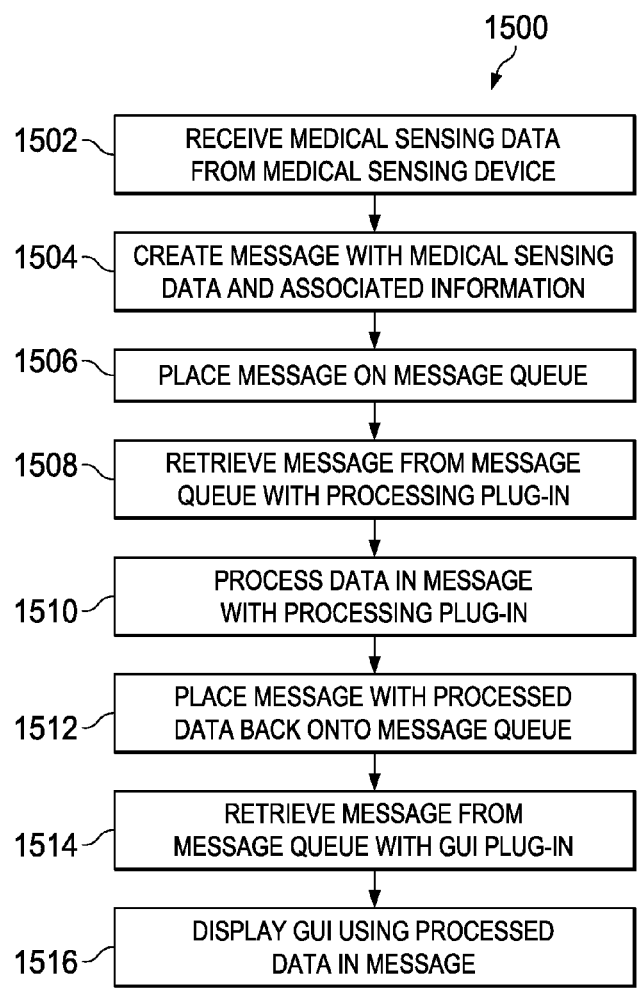
FIG. 17 is a high-level flowchart illustrating a method of processing medical sensing data in the multi-modality processing system.

FIG. 17 is a high-level flowchart illustrating a method 1500 of processing medical sensing data in multi-modality processing system 1401. More specifically, method 1500 describes the manner in which data messages flow within modular architecture of the processing system 1401. For the sake of clarity, the following example will focus on the acquisition of IVUS data, but may similarly apply to other sensing modalities supported by processing system 1401. Method 1500 begins at block 1502 where a stream of unprocessed IVUS data from the IVUS PIM 1412 is received by the IVUS data acquisition module 1436. In this example, IVUS data was digitized by the IVUS PIM 1412 and thus arrives in digital form. Method 1500 proceeds to block 1504 where the IVUS data acquisition module 1436 packetizes the data stream. Specifically, the data acquisition module 1436 creates a plurality of messages that contain a portion of the data, information identifying the modality of the data, and a timestamp. Next, method 1500 continues to block 1506, where the IVUS data acquisition module 1436 places the IVUS messages on the message queue 1446. Then, in block 1508, the IVUS processing plug-in in the software layer 1450 retrieves the IVUS messages from the message queue 1446 in the order in which they were placed on the bus (i.e. FIFO). Method 1500 then proceeds to block 1510 where the IVUS processing plug-in extracts the IVUS data from the messages, interprets the data, and renders IVUS images using the APIs exposed by the processing software stack 1448. Next, in block 1512, the IVUS processing plug-in re-packetizes the processed IVUS data and places it back on the message queue 1446. In some embodiments, the IVUS plug-in also transmits the processed IVUS images to be archived in a storage device such as PACS server 1427. Method 1500 then proceeds to block 1514 where the IVUS GUI plug-in in the software layer 1454 retrieves the messages containing processed IVUS data from the message queue 1446 in the order in which they were placed into the bus by the IVUS processing plug-in. Finally, method 1500 proceeds to block 1516 where the IVUS GUI plug-in extracts the IVUS image data and displays it as part of the IVUS workflow GUI on the bedside control surface 1418 or other controller. Again, the IVUS message flow described above is just an example, but it may be representative of the message flow of data associated with other sensing modalities in processing system 1401.

Figure 18:
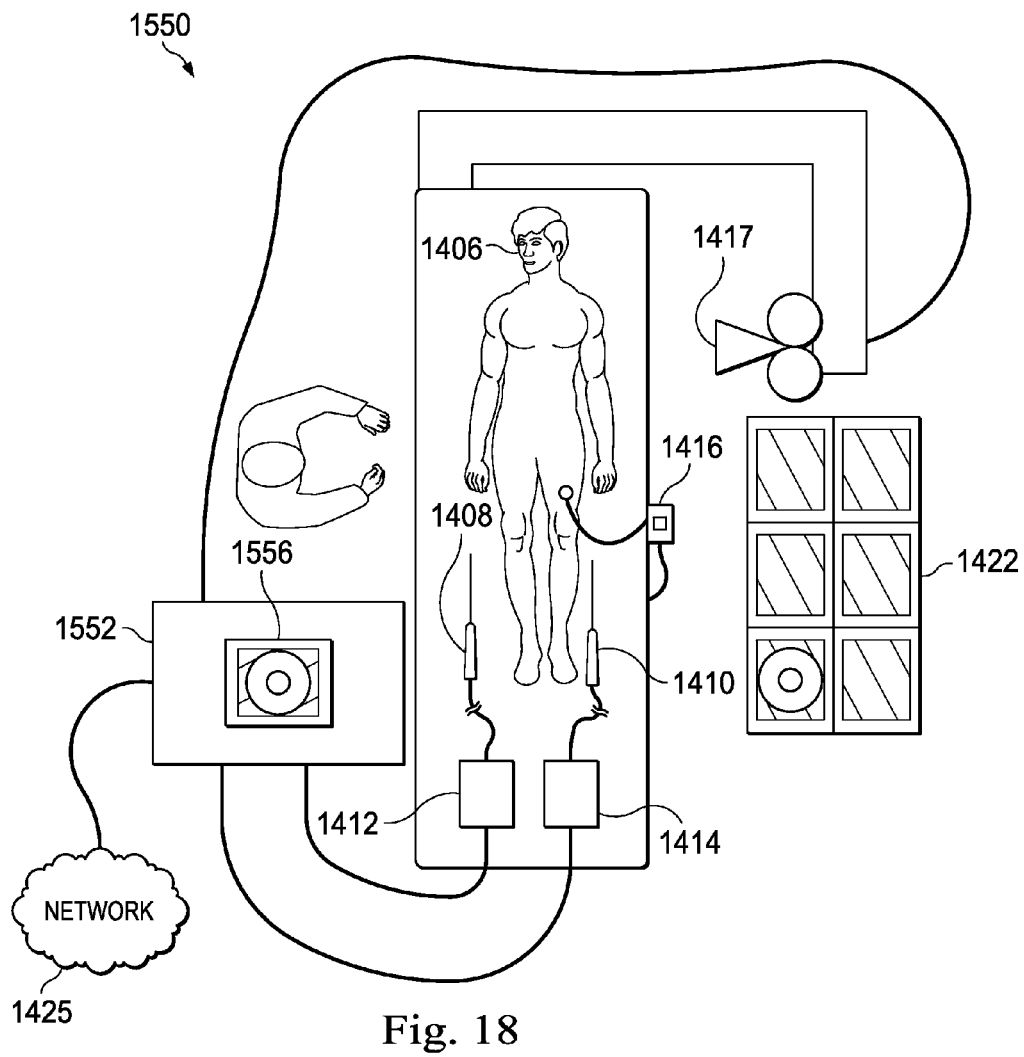
FIG. 18 is a schematic drawing depicting a medical sensing system including a multi-modality processing system according to another embodiment of the present disclosure.
Figure 19:
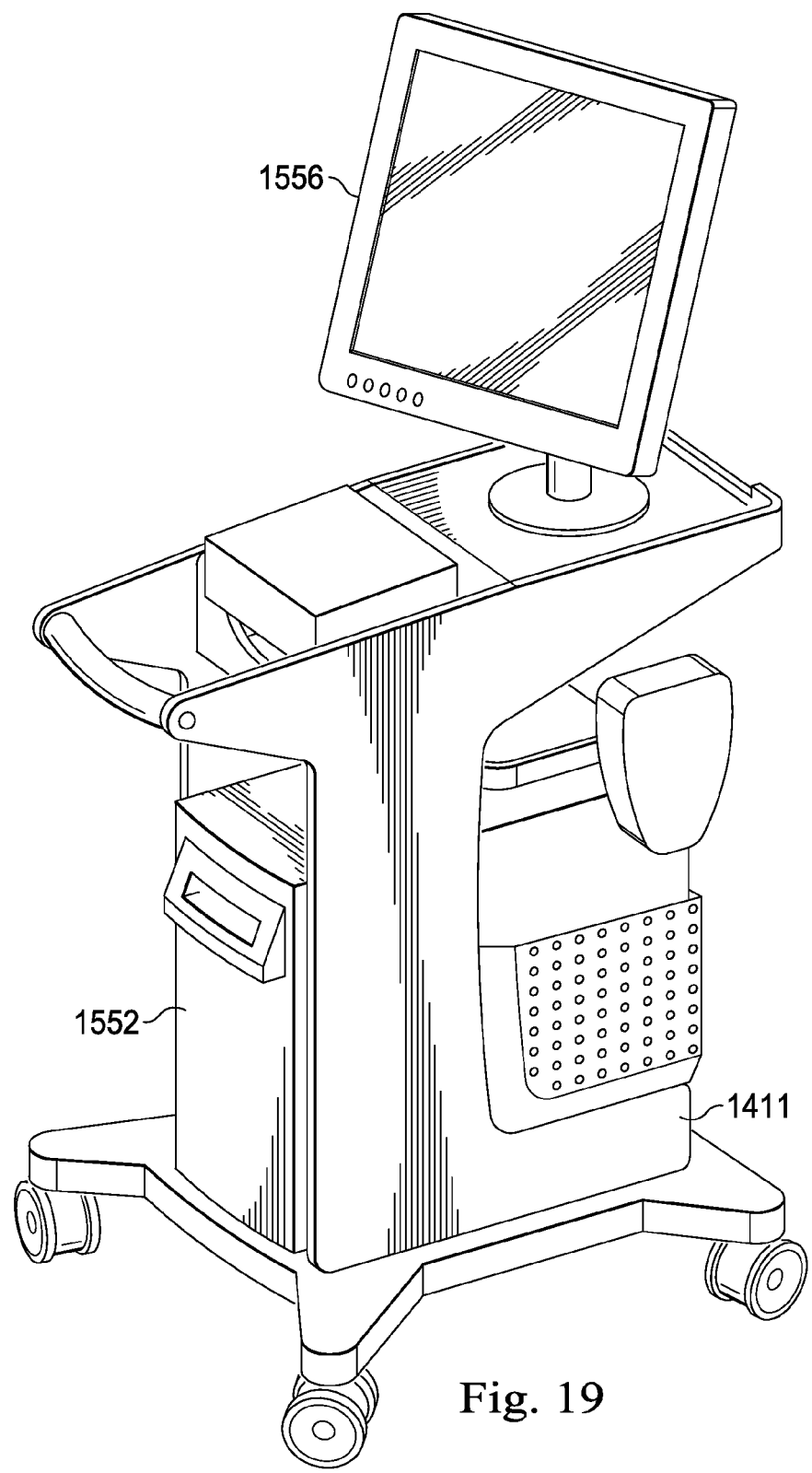
FIG. 19 is a diagrammatic perspective view of an aspect of the medical sensing system of FIG. 18, namely, the multi-modality processing system.

With reference now to FIGS. 18 and 19, FIG. 18 is a schematic drawing depicting a medical sensing system 1550 including a multi-modality processing system 1552 according to another embodiment of the present disclosure. FIG. 19 is a diagrammatic perspective view of the multi-modality processing system 1552 of FIG. 18.

Like the processing system 1401 in system 1400, the multi-modality processing system 1552 in medical sensing system 1550 is an integrated device for the acquisition, control, interpretation, and display of multi-modality medical sensing data. In this regard, the processing system 1550 contains a similar software framework as processing system 1401 (as shown in FIG. 15). However, the processing system 1552 is mobile and may be moved between catheter labs. In the illustrated embodiment, the processing system 1550 is currently located in catheter lab 1402 to perform an IVUS and OCT workflow on patient 1406. In the medical sensing system 1550, the IVUS PIM 1412, OCT PIM 1414, ECG system 1416, angiography system 1417, boom display 1422, and data network 1425 are communicatively coupled to the processing system 1550. Although the medical sensing tools in system 1550 are shown as communicatively coupled to each other and the processing system 1552 via a wired connection (e.g. standard copper link, a fiber optic link), the tools may be connected to the processing system 1552 via wireless connections (e.g. IEEE 802.11 Wi-Fi, UWB, wireless FireWire, wireless USB) in other embodiments.

Further, as shown in FIG. 19, the processing system 1552 sits on a wheeled cart 1554 to facilitate the mobility of the system. In some embodiments, the cart 1554 may include wire management systems to control the various wires attached to the system 1552. Additionally, a controller 1556 sits on the cart 1554 and is communicatively coupled to the processing system 1552. The controller 1556 is operable to present a GUI to a clinician conducting a workflow. In the illustrated embodiment, the controller 1556 is a touch screen that provides user controls and diagnostic images on a single surface. In alternative embodiments, however, the controller 1556 may include both a non-interactive display and separate controls such as physical buttons and/or a joystick.

Although illustrative embodiments have been shown and described, a wide range of modification, change, and substitution is contemplated in the foregoing disclosure and in some instances, some features of the present disclosure may be employed without a corresponding use of the other features. For example, in some embodiments, the medical sensing communication system 100 may be used to process non-cardiovascular diagnostic data such as data from cranial or peripheral arteries, as well as data from non-vascular body portions. Further, the system 100 may be used to collect and process MRI data, or may be utilized in computer assisted surgery (CAS) applications. And, as such, the hub 101 may be configured to communicatively couple medical tools related to non-cardiovascular diagnostic data collection and analysis to a remote processing system. In this regard, the hub 101 may include any number of different and/or additional connector types, links, and internal modules related to any number of medical fields. Further, any number of additional mounting brackets may be coupled to the hub 101 to position it in any number of positions within a medical procedure room or laboratory. Similarly, in some embodiments, the multi-modality processing systems 1401 and 1552 may be used to process non-cardiovascular diagnostic data such as data from cranial or peripheral arteries, as well as data from non-vascular body portions. Further, the systems 1401 and 1552 may be used to collect and process MRI data, or may be utilized in computer assisted surgery (CAS) applications. Further, the modules described above in association with the multi-modality processing systems may be implemented in hardware, software, or a combination of both. And the processing systems may be designed to work on any specific architecture. For example, the systems may be executed on a single computer, local area networks, client-server networks, wide area networks, internets, handheld and other portable and wireless devices and networks. It is understood that such variations may be made in the foregoing without departing from the scope of the present disclosure. Accordingly, it is appropriate that the appended claims be construed broadly and in a manner consistent with the scope of the present disclosure. It is understood that such variations may be made in the foregoing without departing from the scope of the present disclosure. Accordingly, it is appropriate that the appended claims be construed broadly and in a manner consistent with the scope of the present disclosure.

What is claimed is:

1. A medical sensing system, comprising: a first data acquisition module associated with a first medical sensing modality and operable to receive first patient data associated with the first medical sensing modality from a first medical sensing device including a flexible elongate member sized and shaped for insertion into a vessel of a patient body, wherein the first medical sensing modality is an intravascular sensing modality, the first data acquisition module being operable to packetize the first patient data and being one of a plurality of data acquisition modules associated with a plurality of medical sensing modalities, wherein a second data acquisition module of the plurality of data acquisition modules is associated with a second medical sensing modality of the plurality of medical sensing modalities;

a first processing module associated with the first medical sensing modality and operable to process the packetized first patient data;
a first user interface module associated with the first medical sensing modality and operable to present the processed packetized first patient data within a first graphical user interface; and
a message queue module in communication with the first data acquisition module, the first processing module, the first user interface module, and the second data acquisition module to facilitate a multi-modality medical sensing procedure associated with both the first medical sensing modality and the second medical sensing modality, the message queue module being operable to receive the packetized first patient data from the first data acquisition module, temporarily store the packetized first patient data, and make the packetized first patient data available for retrieval by the first processing module;
wherein the second medical sensing modality is different from the first medical sensing modality.

2. The medical sensing system of claim 1,
wherein the second data acquisition module is operable to receive second patient data associated with the second medical sensing modality from a second medical sensing device and to packetize the second patient data,
wherein the system further comprises:
a second processing module associated with the second medical sensing modality and operable to process the packetized second patient data, the second processing module being one of a plurality of processing modules; and
a second user interface module associated with the second medical sensing modality and operable to present the processed packetized second patient data within a second graphical user interface, the second user interface module being one of a plurality of user interface modules,
wherein the first processing module is one of the plurality of processing modules, and
wherein the first user interface module is one of the plurality of user interface modules.

3. The medical sensing system of claim 2, wherein the first and second processing modules are operable to process the respective first and second patient data concurrently.

4. The medical sensing system of claim 1, wherein the first data acquisition module, the first processing module, and the first user interface module are each in communication with the message queue module via application programming interfaces.

5. The medical sensing system of claim 1, wherein the first medical sensing modality is one of intravascular ultrasound (IVUS) imaging, intravascular photoacoustic (IVPA) imaging, optical coherence tomography (OCT), forward looking IVUS (FL-IVUS), fractional flow reserve (FFR), and coronary flow reserve (CFR).

6. The medical sensing system of claim 1, including a second processing module associated with a plurality of medical sensing modalities and operable to process packetized patient data from more than one of the plurality of data acquisition modules.

7. The medical sensing system of claim 1, wherein the first data acquisition module is operable to associate identifying information with the packetized first patient data.

8. The medical sensing system of claim 7, wherein the identifying information includes a timestamp.

9. The medical sensing system of claim 7, wherein the identifying information includes information identifying the first medical sensing modality.

10. The medical sensing system of claim 1, including a processing stack operable to expose an application programming interface to the plurality of processing modules including the first and second processing modules.

11. The medical sensing system of claim 10, wherein the processing stack is configured so that the plurality of processing modules are independent of each other in that additional processing modules may be added to the plurality of processing modules without change to existing processing modules in the plurality of processing modules or the processing stack.

12. The medical sensing system of claim 1, including a user interface stack operable to expose an application programming interface to the plurality of user interface modules including the first and second user interface modules.

13. The medical sensing system of claim 12, wherein the user interface stack is configured so that the plurality of user interface modules are independent of each other in that additional user interface modules may be added to the plurality of user interface modules without change to existing user interface modules in the plurality of user interface modules or the user interface stack.

14. A method of processing medical sensing data, comprising: receiving first patient data from a first medical sensing device including a flexible elongate member sized and shaped for insertion into a vessel of a patient body, the first patient data being associated with a first medical sensing modality, wherein the first medical sensing modality is an intravascular sensing modality;
receiving second patient data from a second medical sensing device, the second patient data being associated with a second medical sensing modality;
creating a first plurality of messages, wherein each message in the first plurality of messages contains a portion of the first patient data;
queuing the first plurality of messages on a message queue;
retrieving the first plurality of messages from the message queue;
processing the first patient data contained in the first plurality of messages;
processing the second patient data associated with the second medical sensing modality;
creating a second plurality of messages wherein each message in the second plurality of messages contains a portion of the processed first patient data;
queuing the second plurality of messages on the message queue; retrieving the second plurality of messages from the message queue; and
rendering, within a first graphical user interface, the processed first patient data contained in the second plurality of messages,
wherein the receiving the first patient data, the receiving the second patient data, the processing the first data, and the processing the second data facilitate a multi-modality medical sensing procedure associated with both the first medical sensing modality and the second medical sensing modality;
wherein the second medical sensing modality is different from the first medical sensing modality.

15. The method of processing medical sensing data of claim 14,
wherein the receiving, the creating the first plurality of messages, and the queuing the first plurality of messages are performed by a first data acquisition module associated with the first medical sensing modality;

wherein the retrieving the first plurality of messages, the processing, the creating the second plurality of messages, and the queuing the second plurality of messages are performed by a first processing module associated with the first medical sensing modality; and wherein the retrieving the second plurality of messages and the rendering are performed by a first user interface module associated with the first medical sensing modality.

16. The method of processing medical sensing data of claim 14, wherein the receiving the first patient data includes receiving data collected by inserting the flexible elongate member into the vessel of the patient body.

17. The method of processing medical sensing data of claim 16, wherein the first patient data includes at least one of intravascular ultrasound (IVUS) imaging data, optical coherence tomography (OCT) data, and fractional flow reserve (FFR) data.

18. The method of processing medical sensing data of claim 14, further comprising:
   creating a third plurality of messages, wherein each message in the third plurality of messages contains a portion of the second patient data;
   queuing the third plurality of messages on the message queue;
   retrieving the third plurality of messages from the message queue;
   processing the second patient data contained in the third plurality of messages;
   creating a fourth plurality of messages, wherein each message in the fourth plurality of messages contains a portion of the processed second patient data;
   queuing the fourth plurality of messages on the message queue;
   retrieving the fourth plurality of messages from the message queue; and
   rendering, within a second graphical user interface, the processed second patient data contained in the fourth plurality of messages.

19. The medical sensing system of claim 2, further comprising a co-registration module associated with the first medical sensing modality and the second medical sensing modality and in communication with the message queue, the co-registration module being operable to temporally synchronize the first patient data and the second patient data for the multi-modality medical sensing procedure.

20. The medical sensing system of claim 2, further comprising a co-registration module associated with the first medical sensing modality and the second medical sensing modality and in communication with the message queue, the co-registration module being operable to assign a common timestamp to the first patient data and the second patient data for the multi-modality medical sensing procedure as the first patient data and the second patient data arrive on the message queue.

21. The medical sensing system of claim 2, further comprising a co-registration module associated with the first medical sensing modality and the second medical sensing modality and in communication with the message queue, the co-registration module being operable to synchronize first sampling at the first medical sensing device for first generation of the first patient data and second sampling at the second medical sensing device for second generation of the second patient data.

* * * * *